US008501158B2

(12) United States Patent
Groman et al.

(10) Patent No.: US 8,501,158 B2
(45) Date of Patent: *Aug. 6, 2013

(54) POLYOL AND POLYETHER IRON OXIDE COMPLEXES AS PHARMACOLOGICAL AND/OR MRI CONTRAST AGENTS

(75) Inventors: Ernest V. Groman, Brookline, MA (US); Kenneth G. Paul, Holliston, MA (US); Timothy B. Frigo, Waltham, MA (US); Howard Bengele, Canton, MA (US); Jerome M. Lewis, Mewton, MA (US)

(73) Assignee: AMAG Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/963,308

(22) Filed: Dec. 8, 2010

(65) Prior Publication Data

US 2011/0144054 A1    Jun. 16, 2011

Related U.S. Application Data

(60) Division of application No. 10/410,527, filed on Apr. 9, 2003, now Pat. No. 7,871,597, which is a continuation-in-part of application No. 09/521,264, filed on Mar. 8, 2000, now Pat. No. 6,599,498.

(60) Provisional application No. 60/128,579, filed on Apr. 9, 1999.

(51) Int. Cl.
*A61B 5/055* (2006.01)
*A01N 43/04* (2006.01)
*A61K 31/715* (2006.01)

(52) U.S. Cl.
USPC ............. 424/9.3; 424/9.351; 514/23; 514/54; 514/59

(58) Field of Classification Search
USPC ................................. 424/9.3; 514/23, 54, 59
See application file for complete search history.

(56) References Cited

U.S. PATENT DOCUMENTS

| | | | |
|---|---|---|---|
| 748,024 A | 12/1903 | Stevens | |
| 1,200,902 A | 10/1916 | Tibbles et al. | |
| 2,856,366 A | 10/1958 | Novak et al. | 252/363.5 |
| 2,856,398 A | 10/1958 | Novak | 260/209 |
| 2,862,920 A | 12/1958 | Berger et al. | 260/209 |
| 2,885,393 A | 5/1959 | Herb | 260/209 |
| 3,000,872 A | 9/1961 | Novak | 260/209 |
| 3,022,221 A | 2/1962 | Floramo | |
| 3,151,107 A | 9/1964 | Heckel et al. | 260/209 |
| 3,234,209 A | 2/1966 | Floramo | 260/209 |
| 4,101,435 A | 7/1978 | Hasegawa et al. | 252/62.53 |
| 4,180,567 A | 12/1979 | Herb | 424/180 |
| 4,370,476 A | 1/1983 | Usher et al. | 536/113 |
| 4,452,773 A | 6/1984 | Molday | 424/1.1 |
| 4,770,183 A | 9/1988 | Groman et al. | 128/654 |
| 4,827,945 A | 5/1989 | Groman et al. | 128/653 |
| 4,933,191 A | 6/1990 | Pucci et al. | 426/48 |
| 5,055,288 A | 10/1991 | Lewis et al. | 424/9 |
| 5,076,950 A | 12/1991 | Ullman et al. | 252/62.51 |
| 5,102,652 A | 4/1992 | Groman et al. | 424/9 |
| 5,128,121 A | 7/1992 | Berg et al. | 424/9 |
| 5,160,726 A | 11/1992 | Josephson et al. | 424/9 |
| 5,204,457 A | 4/1993 | Maruno et al. | 536/101 |
| 5,262,176 A | 11/1993 | Palmacci et al. | 424/9 |
| 5,314,679 A | 5/1994 | Lewis et al. | 424/9 |
| 5,427,767 A | 6/1995 | Kresse et al. | 424/9.32 |
| 5,985,245 A | 11/1999 | Golman et al. | 424/9.36 |
| 6,048,515 A | 4/2000 | Kresse et al. | 424/9.322 |
| 6,165,378 A | 12/2000 | Maruno et al. | 252/62.53 |
| 6,291,440 B1 | 9/2001 | Andreasen et al. | 514/59 |
| 6,599,498 B1 | 7/2003 | Groman et al. | 424/9.34 |
| 7,553,479 B2 | 6/2009 | Groman et al. | 424/9.3 |
| 7,871,597 B2 | 1/2011 | Groman et al. | 424/9.3 |

FOREIGN PATENT DOCUMENTS

| | | |
|---|---|---|
| EP | 0 051 701 A1 | 5/1982 |
| EP | 0051707 | 5/1982 |
| EP | 0 186 947 A1 | 7/1986 |
| EP | 0186947 | 7/1986 |
| EP | 0230768 | 3/1992 |
| EP | 0 516 252 A2 | 12/1992 |
| EP | 0516252 | 12/1992 |
| EP | 0315456 | 6/1994 |
| EP | 0450092 | 5/1996 |
| EP | 0928809 | 7/1999 |
| EP | 1 522 318 A2 | 4/2005 |
| EP | 1169062 | 10/2009 |

(Continued)

OTHER PUBLICATIONS

Amer. Sol. Neph., "Dialysis Epidemiology, Outcomes and Clinical Trials," Codes: FC-Free Communications; PD-Poster Discussions; PS-Poster Sessions, Nov. 1997.
N. Anaizi, Ph.D., "Parenteral Iron Supplementation," The Drug Monitor-Parenteral (IV) Iron Supplementation, http://www.thedrugmonitor.com/iron.html, pp. 1-4, May 20, 2003.
Gudrun Briseid et al., "Dextran-Induced Anaphylactoid Reaction in Man: Altered Reactivity of High Molecular Weight Kininogen," Acta Pharmacol Et. Toxicol, vol. 47, pp. 119-126, 1980.
J. J. Bullen, "The Significance of Iron in Infection," Reviews of Infectious Diseases, vol. 3, pp. 1127-1138, 1981.
Jeff W.M. Bulte, PhD et al., "Short- vs. Long-Circulating Magnetoliposomes as Bone Marrow-Seeking MR Contrast Agents," Journal of Magnetic Resonance Imaging, vol. 9, pp. 329-335, 1999.

(Continued)

*Primary Examiner* — Layla Soroush
(74) *Attorney, Agent, or Firm* — Goodwin Procter LLP

(57) ABSTRACT

Pharmacological compositions, and methods for administration, of the type employing an iron oxide complex with a polyol or polyether. The methods of administration may comprise parenteral administration of an effective dose of the complex formulated in a biocompatible liquid delivered at a rate of from about 1 mL/sec to less than 1 mL/min and wherein upon administration the complex provides minimal detectable free iron in a subject, and minimal incidence of anaphylaxis. The pharmacological compositions are of the type employing a polyol or polyether iron oxide complex, which, upon parenteral administration to a subject, are substantially immunosilent, provide minimal anaphylaxis and minimal free iron, and undergo minimal dissolution in vivo.

2 Claims, 13 Drawing Sheets

FOREIGN PATENT DOCUMENTS

| GB | 1019513 | 2/1966 |
|---|---|---|
| WO | WO 91/09678 | 7/1991 |
| WO | WO 91/12526 | 8/1991 |
| WO | WO 95/05669 | 2/1995 |
| WO | 96/04017 A1 | 2/1996 |
| WO | WO 96/04017 | 2/1996 |
| WO | WO 96/09840 | 4/1996 |
| WO | WO 98/08899 | 3/1998 |
| WO | WO 00/30657 | 6/2000 |
| WO | WO 00/61191 | 10/2000 |
| WO | WO 02/32404 | 4/2002 |

OTHER PUBLICATIONS

P. J. Evans et al., "Measurement of Iron and Copper in Biological Systems: Bleomycin and Copper-Phenanthroline Assays," Methods in Enzymology, vol. 233, pp. 92-92, 1994.

Clive Froud, "Letter to European Patent Office," filing replacement pp. 1-8, 54 and 55, dated Jan. 23, 2007, 5 pages.

Jan Grimm et al., Characterization of ultrasmall, paramagnetic magnetite particles as superparamagnetic contrast agents in MRI, Invest. Radiol., vol. 35(9), pp. 553-556, 1 page.

John M. C. Gutteridge, et al., "Radical-promoting Loosely-bound Iron in Biological Fluids and the Bleomycin Assay," Life Chemistry Reports, vol. 4, pp. 113-142, 1987.

M. K. Hamdy et al., "Light-Scattering, Intrinsic Viscosity, and Gold Number Relationships for Some Dextran Fractions," The Ohio Journal of Science, vol. 58(3), pp. 177-181, May 1958.

C.H. Hanna et al., Effect of Ether and Barbiturate Anesthesia on the Reaction of Rats to Dextran and of Dogs to Polyvinylpyrrolidone, Am. J. Physiol., vol. 191(3), pp. 615-620, 1957.

Masakatsu Hasegawa et al., "Biological Behavior of Dextran-Iron Oxide Magnetic Fluid Injected Intravenously in Rats," Japan J. Appl. Phys. vol. 37, pp. 1029-1032, 1998.

Makoto Hattori et al., "Reduced Immunogenicity of Beta-Lactoglobulin by Conjugation with Carboxymethyl Dextran," Bioconjugate Chem., vol. 11, pp. 84-93, 2000.

Harriet Hedin et al., "Prevention of Dextran Anaphylaxis," Int. Arch Allergy Immunol, vol. 113, pp. 358-359, 1997.

Chong K. Jue et al., "Determination of reducing sugars in the nanomole range with tetrazolium blue," Journal of Biochemical and Biophysical Methods, vol. 11, pp. 109-115, 1985.

Richard A. Kitchen et al., "Total Polysaccharide Test and Quantitative Method for Dextran Analysis," Sugar Processing Research Conference, pp. 232-247, 1983.

Kazuo Kobayashi et al., "Modulation of the T Cell Response to Beta-Lactaglobulin by Conjugation with Carboxymethyl Dextran," Bioconjugate Chem., vol. 14, pp. 168-176, 2003.

Krishan Kumar, "Iron Assay and Size Exclusion High Performance Liquid Chromatography of Ferritin and Magnetoferritin," J. Liq. Chrom. & Rel. Technol., vol. 20(20), pp. 3351-3364, 1997.

Sanda I. Patruta et al., "Neutrophil Impairment Associated with Iron Therapy in Hemodialysis Patients with Functional Iron Deficiency," Journal of the American Society of Nephrology, pp. 655-663, 1998.

John R. Squire et al., "Dextran, Its Properties and Use in Medicine," Charles C. Thomas Publisher, Springfield, IL, 1955.

Sweder van Asbeck et al., "Effect of Iron (III) in the Presence of Various Ligands on the Phagocytic and Metabolic Activity of Human Polymorphonuclear Leukocytes," The Journal of Immunology, vol. 132, No. 2, pp. 851-856, Feb. 1984.

Arthur B. Voorhees et al., "Reactions of Albino Rats to Injections of Dextran," Pro. Soc. Exp. Biol. Med., vol. 76(2), pp. 254-256, 1951.

Eugene D. Weinberg, "Iron and Infection," Microbiological Reviews, vol. 42, pp. 45-66, Mar. 1978.

Dr. Jobst Wibbelmann Wuestohoff & Wuesthoff, Observations by a Third Party According to Article 115EPC Concerning European Patent Application No. EP1169062 in the name of Advanced Magnetics, Inc. filed on Mar. 8, 2000, dated Mar. 29, 2006, 4 pages.

A. Wooding et al., "Proteins and Carbohydrates as Alternative Surfactants for the Preparation of Stable Magnetic Fluids," IEEE Transactions on Magnetics, vol. 24, No. 2, pp. 1650-1652, Mar. 1998.

International Searching Authority, International Search Report on the Declaration, International Application No. PCT/US/06047, dated Feb. 2, 2001, 8 pages.

International Preliminary Authority, International Preliminary Examination Report, together with the Written Opinion, International Application No. PCT/US00/06047, dated Oct. 1, 2001, 20 pages.

Herzon Fiesser & Partner, German Language—Opposition filed with EPO Munich regarding European Patent No. EP 1169062 B1, 23 pages, Jul. 21, 2010.

Herzon Fiesser & Partner, English Translation—Opposition filed with EPO Munich regarding European Patent No. EP 1169062 B1, 25 pages, dated Jul. 21, 2010.

Clive Froud & Co Ltd., Patentee's (AMAG Pharmaceuticals, Inc.) Reply to Opposition submitted to the Eurpoean Patent Office, regarding European Patent No. 1169062, 26 pages, dated Dec. 20, 2010.

Feraheme Ferumoxytol Injection, *AMAG Pharmaceuticals, Inc.*, 4 pages, 2009.

National PBM Drug Monograph—Ferumoxytol (Feraheme™), *Ferumoxytol Monograph* 26 pages, Dec. 2009.

Iron Dextran (Imferon®)—Intravenous (IV) Dilution, http://www.globalrph.com/iron_dextran_dilution.html, 4 pages, Apr. 9, 2012.

Dexferrum (Iron Dextran) Injection, Solution [American Regent, Inc.], 8 pages, http://dailymed.nlm.nih.gov/dailymed/drugInfo.cfm?id=51879 Apr. 9, 2012.

INFeD®—About INFeD—Administration, http://ww.infed.com/about-administration.asp 2 pages, Apr. 9, 2012.

Michael Auerbach, MD, FACP, Clinical Experience with Intravenous Iron, *Transfusion Alternatives in Transfusion Medicine*, vol. 9 (Suppl. 2) pp. 26-30, 2007.

James A. Sloand, et al., Safety and Efficacy of Total Dose Iron Dextran Administration in Patients on Home Renal Replacement Therapies, *Peritoneal Dialysis International*, vol. 18, pp. 522-527, 1998.

R.D. Hamstra, et al., Intravenous Iron Dextran in Clinical Medicine, *JAMA*, PubMed—NCBI, (1 page Abstract) http://www.ncbi.nlm.nih.gov./pubmed/6154155, May, 1980.

W.L. St. Peter, et al., Randomized Cross-Over Study of Adverse Reactions and Cost Implications of Intravenous Push Compared with Infusion of Iron Dextran in Hemodialysis Patients, *Am J. Kidney Dis.*, vol. 4: 523-8 (1 page Abstract) http://www.ncbi.nlm.nig.gov/pubmed/8840941 Oct. 28, 1996.

Altmann, Application No. 00914867.7-2404/1169062; Response to Proprietor's Submission to EPO; Sep. 8, 2011; 21 pages.

European Patent Office, Application No. 00914867.7-2404/1169062; Summons of EPO to Oral Proceedings; Dec. 21, 2011; 8 pages.

Altmann, Application No. 00914867.7-2404/1169062; Opponent's Submission to EPO; Jul. 26, 2012; 8 pages.

Froud, Application No. 00914867.7-2404/1169062; Patent Holder Submission to EPO with Exhibits A-U; Aug. 13, 2012; 299 pages.

Altmann, Application No. 00914867.7-2404/1169062; Submission from Opponent to EPO; Oct. 4, 2012; 8 pages.

European Patent Office, Application No. 00914867.7-2404/1169062; Decision in the Opposition dated Nov. 8, 2012; 1 page.

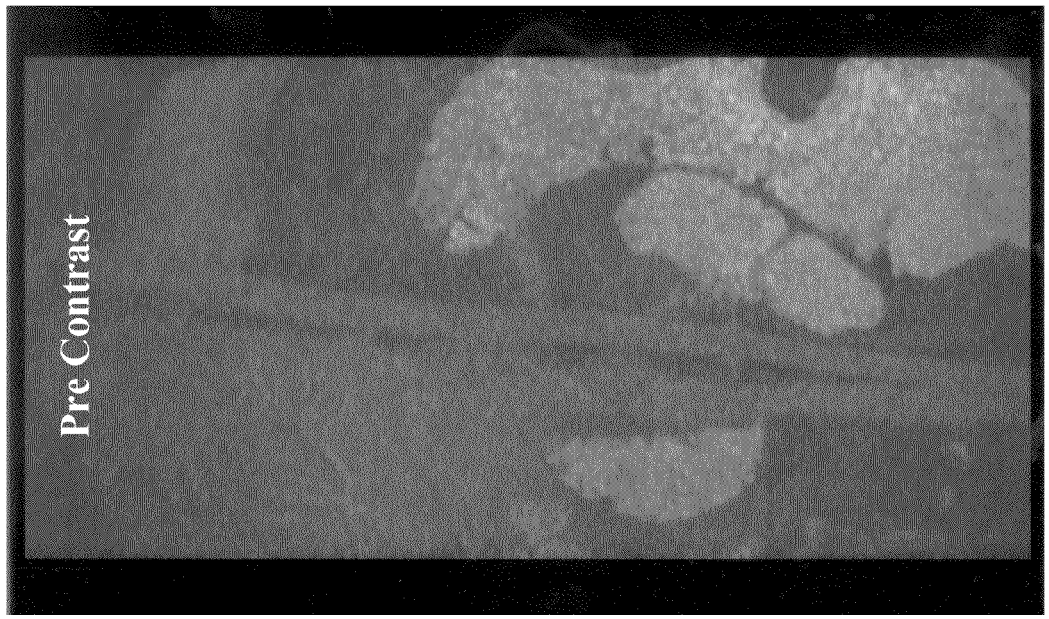

POLYOL AND POLYETHER IRON OXIDE COMPLEXES AS PHARMACOLOGICAL AND/OR MRI CONTRAST AGENTS

CROSS REFERENCE TO RELATED APPLICATIONS

This is a divisional application of application Ser. No. 10/410,527, filed Apr. 9, 2003 now U.S. Pat. No. 7,871,597, which is a continuation-in-part application of U.S. patent application Ser. No. 09/521,264, filed Mar. 8, 2000, now U.S. Pat. No. 6,599,498, which in turn claims the benefit of Provisional Application No. 60/128,579, filed in the United States Patent and Trademark Office on Apr. 9, 1999, all of which are hereby incorporated by reference herein.

TECHNICAL FIELD AND BACKGROUND ART

The field relates to complexes of polyols and polyethers with iron oxides including a reduced polysaccharide or derivatized reduced polysaccharide, and methods for administering as pharmacological and/or MRI contrast agents.

BACKGROUND

Since the invention of magnetic resonance imaging (MRI), a parallel technology of injectable chemicals called contrast agents has developed. Contrast agents play an important role in the practice of medicine in that they help produce more useful MRI images for diagnostic purposes. In particular, two classes of imaging agents have been developed and adopted in clinical practice. These are: low molecular weight gadolinium complexes such as Magnavist®; and colloidal iron oxides such as Feridex I.V.® and Combidex®. Neither of these two types of agents is ideal. Problems encountered with these agents are shown in Table 1, and include: expense of components; inefficiency of synthesis; loss of coating during terminal sterilization (autoclaving); narrow range of organ uptake for purposes of imaging; toxic side-effects; restriction of use to either first pass or equilibrium dosing, and others that are described herein. Agents that overcome these problems, and that combine the properties of these two types of contrast agents, are highly desirable.

TABLE 1

Comparison of ideal properties of MRI contrast agents with properties of low molecular weight gadolinium based contrast agents and colloidal iron oxides.

| Properties of an ideal contrast agent | low molecular weight gadolinium | colloidal iron oxides |
|---|---|---|
| Low production costs: efficient synthesis | Yes | No |
| Autoclavable without excipients | Yes | No |
| T1 agent | Yes | Sometimes |
| T2 agent | No | Yes |
| Non toxic | Yes | No |
| Imaging vascular compartment at early phase (as a bolus administration) and at a late stage (equilibrium phase) | No | No |
| Multiple administration in single examination | No | No |
| Image of multiple target organs | Yes | Sometimes |

TABLE 1-continued

Comparison of ideal properties of MRI contrast agents with properties of low molecular weight gadolinium based contrast agents and colloidal iron oxides.

| Properties of an ideal contrast agent | low molecular weight gadolinium | colloidal iron oxides |
|---|---|---|
| Bolus injection | Yes | No |
| Low volume of injection | No | No |
| Iron source for anemia | No | Yes |

SUMMARY OF THE INVENTION

An embodiment in accordance with the presently claimed invention includes an improved method for administration of a pharmacological composition of the type employing an iron oxide complex with a polyol or polyether, wherein the improvement comprises administering parenterally an effective dose of an iron oxide complex with a polyol or polyether, the complex formulated in a biocompatible liquid so that upon administration the complex provides minimal detectable free iron in a subject and minimal incidence of anaphylaxis, and effecting such administration at a rate substantially greater than 1 mL/min or alternatively, the administration may be at a rate of about 1 mL/sec.

We have found it possible to formulate complexes having the properties described above. Whereas prior art complexes of dextran and iron oxide can be made that have minimal detectable free iron, and other complexes of iron oxide may have minimal incidence of anaphylaxis, no prior art complexes of iron oxide have both properties. We have surprisingly found a way of providing a complex of modified polyols or polyethers with iron oxide that have both properties. We have found, for example, that a polysaccharide such as dextran, when reduced and carboxyalkylated, can be complexed with iron oxide to produce a composition that continues (like dextran iron oxide) to have minimal detectable free iron in a subject, while (unlike dextran iron oxide) also having minimal incidence of anaphylaxis.

Another embodiment of the present invention includes an improved method for administration of a pharmacological composition of the type employing an autoclavable reduced carboxyalkylated polysaccharide iron oxide complex with a polyol or polyether, wherein the improvement comprises administering parenterally an effective dose of an iron oxide complex, the complex formulated in a biocompatible liquid so that upon administration the complex provides minimal detectable free iron in a subject, and minimal incidence of anaphylaxis, and effecting such administration at a rate substantially greater than 1 mL/min or alternatively, a rate of about 1 mL/sec.

A particular embodiment of the presently claimed invention includes an improved method for administration of a pharmacological composition of the type employing an iron oxide complex with a polyol or polyether, wherein the improvement comprises parenteral administration of the complex to provide minimal detectable free iron in a subject as measured by a catalytic bleomycin assay and minimal incidence of anaphylaxis.

Another particular embodiment includes an improved method for administration of a pharmacological composition of the type employing an iron oxide complex with a polyol, for example dextran, or polyether, for example polyethylene glycol, wherein the improvement further comprises parenteral administration of the complex to provide minimal dissolution of the complex in a human subject measured as a function of transferrin saturation in vivo.

Still another particular embodiment provides an improved method for administration of a pharmacological composition of the type employing an iron oxide complex with a polyol or polyether, wherein the improvement further comprises parenteral administration of the complex to provide the polyol or polyether complex as an immunosilent complex in a human subject.

Another particular embodiment in accordance with the present invention includes an improved pharmacological composition of the type employing an iron oxide complex with a polyol or polyether, wherein the improvement comprises formulating a polyol or polyether complexation with iron oxide to provide upon administration to a subject minimal detectable free iron in the subject as measured by a catalytic bleomycin assay and minimal incidence of anaphylaxis.

Yet another embodiment in accordance with the present invention is an improved pharmacological composition of the type employing an iron oxide complex with a polyol or polyether, wherein the improvement comprises formulating a polyol or polyether complex with the iron oxide to provide upon administration to a subject minimal dissolution of the complex in the subject, measured as a function of transferrin saturation in vivo.

Other embodiments include an improved pharmacological composition of the type employing an iron oxide complex with a polyol or polyether, wherein the improvement comprises formulating a polyol or polyether complexation with iron oxide to provide upon administration to a subject the iron oxide complex as an immunosilent complex in a human subject.

Another embodiment in accordance with the present invention includes an improved method for administration of a pharmacological composition of the type employing an iron oxide complex with a polyol or polyether, wherein the improvement comprises parenteral administration of an effective dose of the complex formulated in a biocompatible liquid delivered at a rate substantially greater than 1 mL/min and wherein upon administration the complex provides minimal detectable free iron in a subject, and minimal incidence of anaphylaxis; or alternatively, the complex is delivered at a rate of about 1 mL/sec. More particularly, the improved method may utilize an assay for determining minimal detectable free iron wherein the assay is any assay known in the art for measuring free iron concentration, including a BDI assay, atomic absorption spectroscopy, a % transferrin saturation assay, a % dialysis assay, and a bacterial growth assay. Still more particularly, the assay for determining minimal incidence of anaphylaxis is an ELISA assay.

In other embodiments in accordance with the invention includes an improved method for administering a pharmacological composition of the type employing an iron oxide complex with a polyol or polyether, wherein the improvement comprises parenteral administration of an effective dose of the complex formulated in a biocompatible liquid delivered at a rate substantially greater than 1 mL/min, or alternatively at about 1 mL/sec, and wherein upon administration the complex provides minimal detectable free iron in a subject and minimal incidence of anaphylaxis, and wherein the free iron concentration is determined using a BDI assay, and is less than about 750 nM, or less than about 0.04 µg/mL, or less than about 0.1% of the effective dose of iron oxide, depending upon how the BDI-detected free iron measurement is reported. In alternative embodiments, the free iron concentration is determined using atomic absorption spectroscopy, and is less than about 1 ppm or less than about 0.04 µg/mL, or less than about 0.1% of the effective dose of the iron oxide, depending upon how the atomic absorption-detected free iron measurement is reported; or, the free iron concentration is determined using a iron dialyzed % assay, and the dialyzed-determined free iron percent is less than about 1%.

Yet another embodiment of the present invention includes an improved method for administration of a pharmacological composition of the type employing an iron oxide complex with a polyol or polyether, wherein the improvement comprises parenteral administration of an effective dose of the complex formulated in a biocompatible liquid delivered at a rate substantially greater than 1 mL/min, or alternatively at a rate of about 1 mL/sec, and wherein upon administration the complex provides minimal detectable free iron in a subject and minimal incidence of anaphylaxis, and wherein the improvement further comprises parenteral administration of the complex to provide minimal dissolution of the complex in a human subject. More particularly, in alternative embodiment, the minimal dissolution of the complex is determined using a % transferrin saturation assay; and more particularly, the minimal dissolution of the complex determined by a % transferrin saturation assay is less than about 95% saturation for a total dose from about 1 mg/kg of body weight to about 4 mg/kg of body weight, up to a total single dose of about 500 mg to about 600. An alternative embodiment further comprises parenteral administration of the complex to provide the iron oxide complex as a substantially immunosilent complex in a human subject. In such embodiments, verification of administration that provides a complex that is substantially immunosilent in a human complex may be determined by a guinea pig anaphylaxis test.

Other embodiments in accordance with the present invention include an improved pharmacological composition of the type employing an iron oxide complex with a polyol or polyether, wherein the improvement comprises a polyol or polyether iron oxide complex composition prepared at concentrations of between about 1 mg/kg of body weight to about 4 mg/kg of body weight in a total volume of biocompatible liquid from about 1 mL to about 15 mL and for a total single dose from about 50 mg to about 600 mg, wherein the pharmacological composition is capable of being parenterally administered to a subject at a rate substantially greater than 1 mL/min, or alternatively at a rate of about 1 mL/sec, and wherein the iron oxide complex provides upon administration minimal detectable free iron in the subject and minimal incidence of anaphylaxis. More particularly, the improved pharmacological composition may further comprise an iron oxide complex having minimal free iron concentration in the subject. Determination of minimal free iron can be measured using any standard assay for measuring free iron known in the art, including a BDI assay, atomic absorption spectroscopy, a % transferrin saturation assay, a % dialysis assay, or a bacterial growth assay. Alternatively, the improved pharmacological composition may further comprise an iron oxide complex that undergoes minimal dissolution in a human subject upon administration to the subject. Other alternatives envision that the improved pharmacological composition may further comprise an iron oxide complex that undergoes minimal dissolution upon administration in a human subject. Minimal dissolution may be determined using a % transferrin saturation assay. Alternatively, the improved pharmacological composition may further comprise an iron oxide complex that is substantially immunosilent upon administration in a human subject, and particularly, the improved pharmacological composition may further comprise an iron oxide complex that is substantially immunosilent in a human subject as determined by a guinea pig anaphylaxis test.

Yet another embodiment in accordance with the present invention includes a method of treating a subject with an iron oxide complex to a subject in need thereof, the method comprising parenterally administering the complex formulated in a pharmaceutically acceptable formulation in a biocompatible liquid, effecting administration at a rate substantially greater than 1 mL/min, and providing an effective dose in the range of about 1 mg/kg of body weight to about 4 mg/kg of body weight in a total volume of biocompatible liquid of between about 1 mL and 15 mL so that minimal free iron and minimal anaphylaxis occurs. More particularly, the method may comprise effecting administration at a rate of between about 180 µL/sec and about 1 mL/min. Still more particularly, the administration of the iron oxide complex provides minimal dissolution of the complex in the subject and may further provide a substantially immunosilent complex to the subject. More particularly, a guinea pig test may be used to determine that the complex administered in the above method for treating is substantially immunosilent to the subject.

Another embodiment of the invention includes a method of treating a subject with an autoclavable reduced carboxyalkylated polyol, for example dextran, iron oxide complex having at least 750 but less than 1500 µmole of carboxyalkyl groups per gram of polyol to a subject, the method comprising parenterally administering the complex formulated in a pharmaceutically acceptable formulation in a biocompatible liquid, effecting administration at a rate substantially greater than 1 mL/min, and providing an effective dose in the range of about 1 mg/kg of body weight to about 4 mg/kg of body weight in a total volume of biocompatible liquid of between about 1 mL and 15 mL so that minimal free iron and minimal anaphylaxis occurs.

Yet another embodiment includes an improved pharmacological composition of the type employing an autoclavable carboxyalkylated polyether iron oxide complex, for example polyethylene glycol, wherein the improvement comprises a carboxyalkylated iron oxide complex composition having at least 250 µmole but less than 1500 µmole of carboxyalkyl groups per gram of polyether, prepared at concentrations of between about 1 mg/kg of body weight to about 4 mg/kg of body weight in a total volume of biocompatible liquid from about 1 mL to about 15 mL and for a total single dose from about 50 mg to about 600 mg, wherein the pharmacological composition is capable of being parenterally administered to a subject at a rate substantially greater than 1 mL/min and wherein the iron oxide complex provides upon administration minimal detectable free iron in the subject and minimal incidence of anaphylaxis.

Another embodiment of the invention is a method of providing an iron oxide complex for administration to a mammal subject, the method comprising: producing a reduced polysaccharide iron oxide complex, and sterilizing the complex by autoclaving. In general, the reduced polysaccharide is a reduced polymer of glucose. An example of a reduced polymer of glucose is a reduced dextran. The reduced polysaccharide is produced through reaction of a polysaccharide with a reagent selected from the group consisting of a borohydride salt or hydrogen in the presence of a hydrogenation catalyst. In a further aspect of the method, the iron oxide is superparamagnetic.

Another particular embodiment of the invention is a method of providing an iron oxide complex for administration to a mammalian subject, the method comprising: producing a derivatized reduced polysaccharide iron oxide complex, and sterilizing the complex by autoclaving. According to this method, producing the complex can include derivatizing a reduced polysaccharide by formation of, for example, ethers, amides, esters, and amines at the hydroxyl positions of the polysaccharide. In a particular embodiment, the derivative formed is an ether of the polysaccharide, more particularly a carboxyalkyl ether of the polysaccharide, and more particularly, a carboxymethyl ether of the polysaccharide. Further according to this method, the reduced polysaccharide can be a reduced dextran. The derivatized, reduced polysaccharide can be isolated as the sodium salt and does not contain an infrared absorption peak in the region of 1650-1800 $cm^{-1}$. In one aspect of the method, producing the derivatized reduced polysaccharide is achieved at a temperature of less than approximately 50° C. In another aspect of the method, producing the derivatized reduced polysaccharide is achieved at a temperature of less than approximately 40° C. In a further aspect of the method, the iron oxide is superparamagnetic.

In yet another embodiment, the invention provides a method of formulating an iron oxide complex coated with a reduced polysaccharide. This composition is for pharmacological use and the composition has decreased toxicity in comparison to a formulation of an iron oxide complex coated with the non-reduced polysaccharide. The method of formulating such an iron oxide complex comprises: producing a reduced polysaccharide iron oxide complex, and sterilizing the complex by autoclaving. The formulation provides a polysaccharide which was produced by reacting the polysaccharide with one of a reducing agent selected from the group consisting of a borohydride salt or hydrogen in the presence of an hydrogenation catalyst, wherein the reduced polysaccharide iron oxide complex so made has such decreased toxicity. In a further aspect of the method, the iron oxide is superparamagnetic.

In yet another embodiment, the invention provides a method of formulating an iron oxide complex coated with a reduced derivatized polysaccharide. This composition is for pharmacological use and the composition has decreased toxicity in comparison to a formulation of an iron oxide complex coated with the non-reduced derivatized polysaccharide. The method of formulating such an iron oxide complex comprises: producing a reduced derivatized polysaccharide iron oxide complex; and sterilizing the complex by autoclaving. According to this method, producing the complex can include derivatizing a reduced polysaccharide by carboxyalkylation, for example, wherein the carboxyalkylation is a carboxymethylation. Further according to this method, the reduced polysaccharide can be a reduced dextran. The derivatized, reduced polysaccharide can be isolated as the sodium salt and does not contain an infrared absorption peak in the region of 1650-1800 $cm^{-1}$. In one aspect of the method, producing the derivatized reduced polysaccharide is achieved at a temperature of less than approximately 50° C. In another aspect of the method, producing the derivatized reduced polysaccharide is achieved at a temperature of less than approximately 40° C. In a further aspect of the method, the iron oxide is superparamagnetic.

Another embodiment of the invention provides a reduced derivatized polysaccharide iron oxide complex with T1 and T2 relaxation properties to allow contrast agent signal enhancement with T1 sequences and signal diminishment with T2 sequences. A further aspect of the embodiment is that the reduced derivatized polysaccharide iron oxide can be administered multiple times for sequential imaging in a single examination. Yet another aspect of the agent is that it can be used to image multiple organ systems including the vascular system, liver, spleen, bone marrow, and lymph nodes.

Another embodiment of the invention provides a reduced polysaccharide iron oxide complex for use as an intravenous iron supplement.

Another embodiment of the invention provides a reduced derivatized polysaccharide iron oxide complex for use as an intravenous iron supplement.

In yet a further embodiment, the invention provides an improved method of administering to a mammalian subject an autoclaved reduced polysaccharide iron oxide complex. The improved method of administration comprising: injection of an autoclaved reduced polysaccharide iron oxide complex in a volume of 15 mL or less. In another aspect of the embodiment the injected volume is injected as a bolus. In a further aspect of the method, the iron oxide is superparamagnetic. In a further aspect of the embodiment the injected volume provides improved image quality.

In yet a further embodiment, the invention provides an improved method of administering to a mammalian subject an autoclaved derivatized reduced polysaccharide iron oxide complex, the improved method of administration comprising: injection of an autoclaved reduced derivatized polysaccharide iron oxide complex in a volume of 15 mL or less. In another aspect of the embodiment the injected volume is injected as a bolus. In a further aspect of the method, the iron oxide is superparamagnetic. In a further aspect of the embodiment the injected volume provides improved image quality.

An embodiment of the invention provides an improved method of administering to a mammalian subject a reduced polysaccharide iron complex to a mammalian subject wherein the improvement comprises administration of a reduced polysaccharide in formulation to provide reduced toxicity relative to administration of a non-reduced polysaccharide. In a further aspect of the embodiment, the iron oxide is superparamagnetic.

An embodiment of the invention provides an improved method of administering to a mammalian subject a reduced derivatized polysaccharide iron complex in a manner that the composition provides reduced toxicity, wherein the improvement comprises utilizing a reduced derivatized polysaccharide in formulation of the composition. In a further aspect of the embodiment, the iron oxide is superparamagnetic.

An embodiment of the invention provides a reduced polysaccharide iron oxide complex, wherein the reduced polysaccharide is derivatized, for example, the reduced derivatized polysaccharide is a carboxyalkyl polysaccharide. The carboxyalkyl is selected from the group consisting of carboxymethyl, carboxyethyl and carboxypropyl. Further, the reduced polysaccharide can be a reduced dextran, for example, the reduced dextran can be a reduced carboxymethyl dextran. A further aspect of this embodiment of the invention is that the level of derivatization of the reduced dextran is at least 750 µmole but less than 1500 µmole of carboxyl groups per gram of polysaccharide wherein said composition has reduced toxicity relative to composition with respect to lower levels of derivatization.

An embodiment of the invention provides a reduced polysaccharide iron oxide complex, such complex being stable at a temperature of at least approximately 100° C. In a preferred embodiment, such complex is stable at a temperature of approximately 121° C. In an even more preferred aspect of the reduced polysaccharide iron oxide complex, such complex is stable at a temperature of at least 121° C. for a time sufficient to sterilize the complex. In a further aspect of the embodiment, the iron oxide is superparamagnetic.

An embodiment of the invention provides a reduced derivatized polysaccharide iron oxide complex, such complex being stable at a temperature of at least approximately 100° C. In a preferred embodiment, such complex is stable at a temperature of approximately 121° C. In an even more preferred aspect of the reduced polysaccharide iron oxide complex, such complex is stable at a temperature of at least 121° C. for a time sufficient to sterilize the complex. In a further aspect of the embodiment, the iron oxide is superparamagnetic.

A particular embodiment of the invention is a method of formulating for pharmacological use a reduced polysaccharide iron oxide complex having increased pH stability in comparison to the corresponding native dextran iron oxide, the method comprising: providing dextran; and reacting the dextran with a borohydride salt or hydrogen in the presence of an hydrogenation catalyst, reacting the reduced dextran with iron salts to provide a formulation having a stable pH.

A particular embodiment of the invention is a method of formulating for pharmacological use a reduced derivatized polysaccharide iron oxide complex having increased pH stability in comparison to the corresponding native dextran iron oxide, the method comprising: providing dextran; and reacting the dextran with a borohydride salt or hydrogen in the presence of an hydrogenation catalyst, reacting the reduced dextran with iron salts to provide a formulation having a stable pH.

In another embodiment, the invention provides a method of formulating a reduced derivatized dextran composition for pharmacological use wherein the composition has decreased toxicity in comparison to native dextran, comprising: producing a reduced derivatized polysaccharide; and sterilizing the product by autoclaving. According to this method, the reduced polysaccharide is obtained by reacting the native polysaccharide with one of several reducing agents selected from the group consisting of a borohydride salt or hydrogen in the presence of a hydrogenation catalyst. In a preferred aspect of the embodiment the polysaccharide is dextran. Producing the composition can include derivatizing a reduced polysaccharide by carboxyalkylation, for example, wherein the carboxyalkylation is a carboxymethylation. Further according to this method, the reduced polysaccharide can be a reduced dextran. The derivatized, reduced polysaccharide can be isolated as the sodium salt and does not contain an infrared absorption peak in the region of 1650-1800 $cm^{-1}$. In one aspect of the method, producing the derivatized reduced polysaccharide is achieved at a temperature of less than approximately 50° C. In another aspect of the method, producing the derivatized reduced polysaccharide is achieved at a temperature of less than approximately 40° C.

An embodiment of the invention provides an improved method of administering a polysaccharide to a mammalian subject, wherein the improvement comprises parenteral administration of a reduced polysaccharide in a formulation to provide reduced toxicity relative to administration of a non-reduced polysaccharide.

An embodiment of the invention provides a reduced polysaccharide, wherein the reduced polysaccharide is derivatized, for example, the reduced derivatized polysaccharide is an ether-, amino-, ester-, and amido-polysaccharide. In a more particular embodiment, the reduced derivatized polysaccharide is an ether polysaccharide, more particularly a carboxyalkylether polysaccharide selected from the group consisting of carboxymethylether, carboxyethylether, and carboxypropylether polysaccharide. Further, the reduced polysaccharide can be a reduced dextran. A further aspect of this embodiment of the invention is that the level of derivatization of the reduced dextran is at least 750 micromolar of carboxyl groups per gram of polysaccharide wherein said composition has reduced toxicity relative to composition with lower levels of derivatization.

Another embodiment of the invention is a method of formulating a dextran composition for pharmacological use having decreased toxicity in comparison to native dextran, the method comprising: providing dextran; and reacting the provided dextran with a borohydride salt or hydrogen in the presence of an hydrogenation catalyst followed by carboxyalkylation, the reduced carboxyalkylated dextran having decreased toxicity.

Another embodiment of the invention is an improved method of administering to a mammalian subject a derivatized polysaccharide dextran composition wherein the improvement comprises parenteral administration of a reduced carboxyalkylated dextran in a formulation to provide reduced toxicity relative to administration of a non-reduced non-carboxyalkylated dextran. In another aspect, an embodiment of the invention is an improved method of administering to a mammalian subject a derivatized polysaccharide dextran composition wherein the improvement comprises parenteral administration of a reduced carboxymethylated dextran in a formulation to provide reduced toxicity relative to administration of a non-reduced non-carboxymethylated dextran.

An embodiment of the invention provides a method of use of reduced derivatized dextrans as blood expanders.

The above-described embodiments are merely illustrative and not intended to limit the invention in any way. It is envisioned that other embodiments are possible and will be understood to fall within the scope of the presently claimed invention.

DETAILED DESCRIPTION OF SPECIFIC EMBODIMENTS

Figure 1:
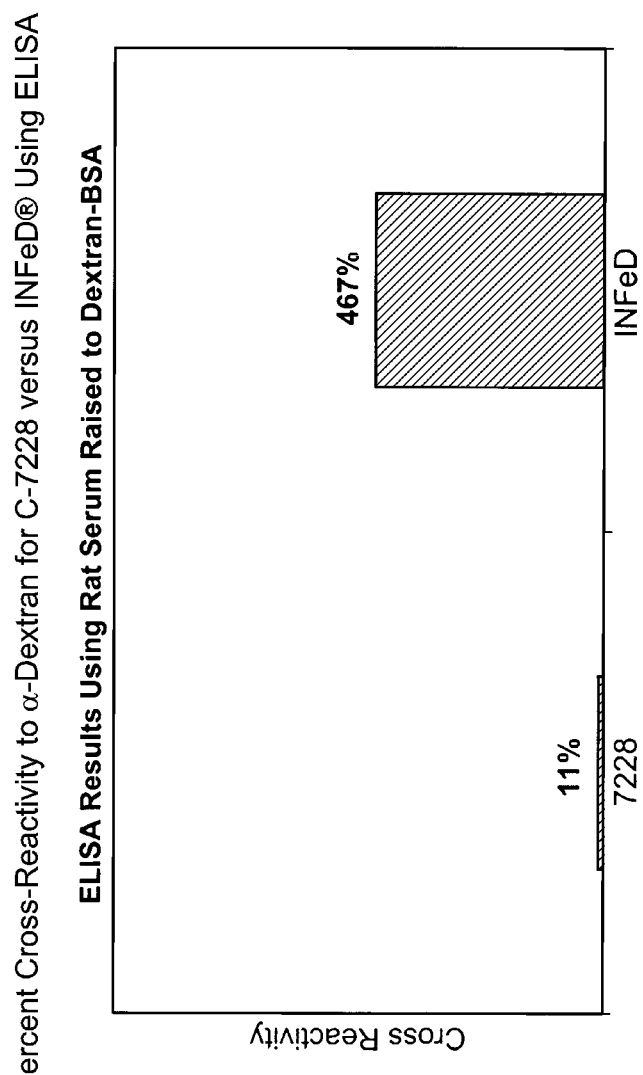
FIG. 1 is a graph that shows the percent of cross-reactivity observed with compound 7228 in accordance with the present invention, as compared to percent cross-reactivity observed with InFeD® using a rat serum α-Dextran Antibody ELISA assay. The graph is plotted from the date of Table 2.

As used in this description and the accompanying claims, the following terms shall have the meanings indicated, unless the context otherwise requires:

"Minimal detectable free iron as measured by a catalytic bleomycin assay" means, within the context of this invention, bleomycin detectable iron (BDI) from 0 nM to about 750 nM, or from 0 μg/mL to about 0.04 μg/mL, or from 0% to about 0.1% of the dose, depending upon how the measurement is reported.

"Minimal detectable free iron as measured by atomic absorption spectrophotometry" means, within the context of this invention, free iron of from 0 ppm to less than about 1 ppm, or from 0 mg/g to less than about 0.02 mg/g, or from 0% to less than about 0.1% (mg/mL as determined by AA, divided by total iron concentration of original sample), depending upon how the measurement is reported.

"Minimal detectable free iron as measure by an iron dialyzed % assay" is from about 0% to less than about 1%.

"Minimal dissolution of the complex, measured as a function of transferrin saturation in vivo", means within the context of this invention that at total doses from 1 mg to about 500 mg total dose, transferrin saturation remains less than about 95%.

"Minimal incidence of anaphylaxis" means, within the context of this invention, incidence from 0 to less than about 0.01% to about 0.05% of acute systemic sensitivity reactions, anaphylactoid reactions or severe anaphylactic shock, including death.

"Case fatality rate" means total number of fatalities per total number of allergic reactions, expressed as a percent.

"An administration rate of about 1 mL/sec" as used herein, is defined as a rate of 0.1 mL/sec to 3 mL/sec.

"Rapid intravenous injection" as used here in, is defined as injection with a delivery rate of about 1 mL/sec, as defined above.

"Biocompatible liquid" as used herein, is defined as any liquid that can be administered to a mammalian subject and that is tolerated by the mammalian subject, as evidence by a dearth of adverse reactions. Examples of biocompatible liquids include water, buffered aqueous media, saline, buffered saline, aqueous Zwitter ion solutions, low-molecular weight alcohols, amino acids, mixtures thereof, and the like.

"Heat stress" as used herein and in the accompanying claims, is defined as heating the colloid to approximately 121° C. or higher for about 30 minutes at neutral pH, or other combinations of time, temperature, and pH that are well known in the art to autoclave (or terminally sterilize) an injectable drug.

"Colloid" as used in this specification and the accompanying claims shall include any macromolecule or particle having a size less than about 250 nm.

Table 2 summarizes the percent cross-reactivity observed with compound 7228 (C-7228) of the present invention compared to percent cross-reactivity observed with InFeD®, using a rat serum a-dextran antibody ELISA assay. This assay is used to measure the incidence of anaphylactic response to an iron oxide complex.

Surprisingly, the iron compounds of the present invention have been shown to exhibit superior administration profiles in a subject compared to iron oxide compounds currently approved for either use as a hematinic agent or an MRI contrast agent. Thus, unlike existing iron oxide complexes currently available, polyol or polyether iron oxide complexes in accordance with the present invention, when administered parenterally to a patient for use as a pharmacological agent, provide both minimal detectable free iron in a subject as determined using a bleomycin catalytic assay or measured by atomic absorption spectrophotometry, and provide minimal anaphylaxis in a patient. These iron oxide polyol or polyether complexes may further provide minimal dissolution of the iron complex in a human subject as determined as a function of measurement of percent transferrin saturation, and may present in the human subject as an immunosilent complex to the subject's immune response system. Table 3 shows standard solutions for use in calibrating an atomic absorption spectrophotometer.

Table 4 shows free iron determination tests done on C-7228 compared to other iron oxide complexes currently available.

Table 5 shows Free Iron concentrations, in μM, μg/mL and percentage of the dose, for serum spiked with I.V. iron, as determined using a bleomycin catalytic iron assay.

Table 1 summarizes the characteristics of two classes of MRI contrast agents that have been previously described, and shows a comparison of their characteristics to those of an ideal contrast agent. Agents of the invention embody the ideal characteristics, as shown herein.

Surprisingly, the development and synthesis of preparations of ultrasmall superparamagnetic iron oxide (USPIOs) coated with polysaccharide reduced dextrans and derivatives of reduced dextrans, such as the agents with the desirable properties as shown herein, are derived from a change in the chemical nature of one constituent, dextran T10. This change involved reduction of the terminal aldehyde group to an alcohol of the polysaccharide used in its synthesis to an alcohol (Scheme 1). Scheme 1 illustrates the chemical change in a polysaccharide such as dextran upon treatment with sodium borohydride. The hemiacetal form of the polysaccharide (structure 1) is in equilibrium with the aldehyde form of the polysaccharide (structure 2). Structure 2 represents less than 0.01% of the equilibrium mixture (Brucker, G. (1974) *Organic Chemistry: Amino Acids, Peptides and Carbohydrates*, Tankonykiado Press, Budapest, p. 991). Treatment of structure 2 with sodium borohydride results in its irreversible conversion to the linear polyol form of the polysaccharide (structure 3). The dynamic equilibrium between structures 1 and 2 allows complete conversion, when treated with sodium borohydride, to the linear polyol (structure 3).

Scheme 1:

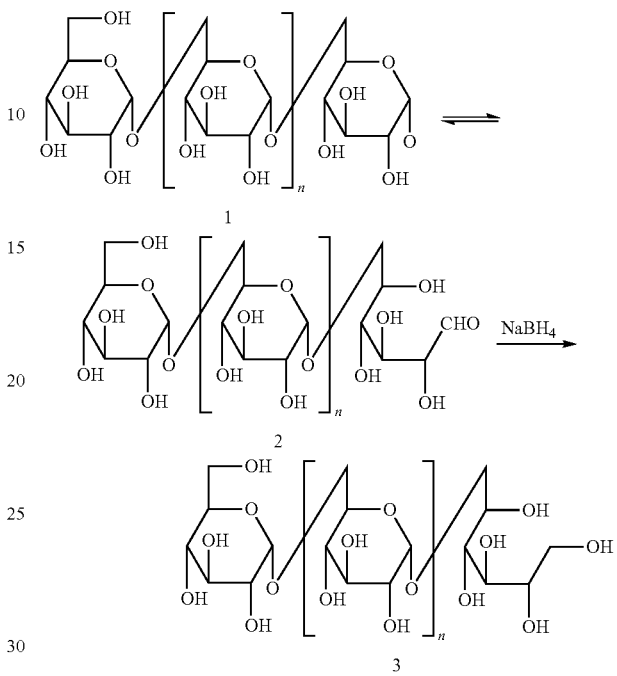

Dextran coated superparamagnetic iron oxide particles have particular interest as magnetic resonance imaging (MRI) contrast agents because of their ability to enhance images of the liver and lymph. Feridex I.V.® (Advanced Magnetics, Inc., Cambridge Mass.) is a dextran coated superparamagnetic iron oxide MRI contrast agent, and approved for use in humans. Combidex® (Advanced Magnetics, Inc.) is a dextran coated ultrasmall superparamagnetic iron oxide (USPIO) which has completed Phase III clinical trials for both liver imaging and Phase III trials for lymph imaging. Combidex® has a smaller mean diameter (20 nm) than Feridex I.V.® (60 nm), which gives it a different biodistribution in humans. Combidex® is made by addition of base to a solution of dextran, ferric chloride and ferrous chloride. The synthetic process comprises combining the ingredients, heating, and purifying by ultrafiltration. However, the yield of dextran added to the particles in the reaction is inefficient. Pharmaceutical grade dextran is the most expensive component of the Combidex® synthesis. A more efficient use of dextran in the synthesis of Combidex® is desirable to lower production costs.

Terminal sterilization (autoclaving) is a preferred method of sterilizing drugs for injection. However, many superparamagnetic iron oxide colloids that are used as MRI contrast agents are synthesized with polymer coatings and coverings that influence the biodistribution and elimination of these colloids. Upon exposure to the heat for the duration of the autoclaving process, the polymer coating can become dissociated from the iron oxide cores. The functional consequences of polymer dissociation from the iron oxide are physical changes in the material, such as clumping, biodistribution changes (changes in plasma half life), and changes in toxicity profile (potential increases in adverse events). For example, a substantial decrease in the pH of the solution can be detected following autoclaving of iron dextran particles, and the pH continues to fall upon further storage.

Several solutions to the problem of imparting resistance to heat stress have been described. Palmacci et al., U.S. Pat. No. 5,262,176, hereby incorporated herein by reference, used cross-linked dextran to stabilize the covering on the iron oxide particles prior to autoclaving. The cross-linking process uses noxious agents such as epichlorohydrin and epibromohydrin, which must be removed from the colloid after the cross-linking reaction.

Methods of preventing clumping of the colloid induced by heat stress that have no effect on coating dissociation have also been described. These methods generally include the use of excipients during the autoclaving process. Groman et al., U.S. Pat. No. 4,827,945, and Lewis et al., U.S. Pat. No. 5,055,288, both patents hereby incorporated herein by reference, use citrate to prevent clumping of the particles when the coating dissociates. However, the use of citrate in high concentrations in combination with heat can cause toxicity. Groman et al., U.S. Pat. No. 5,102,652, hereby incorporated herein by reference, uses low molecular weight carbohydrates such as mannitol to prevent clumping during autoclaving. These excipients increase the cost and complexity of manufacturing the product, yet do not solve the problem of dissociation of the polymer from the iron particle.

Josephson et al., U.S. Pat. No. 5,160,726, hereby incorporated herein by reference, avoids heat stress on the coating by using filter sterilization rather than heat to sterilize the colloid. Filter sterilization is expensive since both the sterilization process and container closure must be performed in a germ free environment. Additionally, filter sterilizing has a higher rate of failure than the process of autoclaving, which reflects the inability to obtain an environment for the filtration step which is entirely germ free.

Maruno et al., U.S. Pat. No. 5,204,457, describes a carboxymethyldextran-coated particle with improved stability up to 80° C. for an extended period but does not teach use of terminal sterilization by autoclaving. Hasegawa et al. (Japan J. Appl. Phys., Part 1, 37(3A):1029-1032, 1998) describes carboxymethyl dextran coated iron particles with thermal stability at 80° C., but does not teach use of a carboxymethyl reduced dextran-coated particle, nor of terminal sterilization by autoclaving.

Magnetic resonance imaging agents act by affecting the normal relaxation times, principally on the protons of water. There are two types of relaxation, one known as spin-spin or T1 relaxation, and the second known as spin-lattice or T2 relaxation. T1 relaxation generally results in a brightening of the image caused by an increase in signal. T1 processes are most useful in imaging of the vascular system. T2 relaxation generally results in a darkening of the image caused by a decrease in signal. T2 processes are most useful in imaging of organs such as the liver, spleen, or lymph nodes that contain lesions such as tumors. All contrast agents have both T1 and T2 properties; however, either T1 or T2 relaxation can characterize the dominant relaxation property of a particular contrast agent. Low molecular weight gadolinium based contrast agents are T1 agents, and have primary application in the imaging of vascular related medical problems such as stroke and aneurysms and the brain. Iron oxide based colloidal contrast agents are T2 agents, and have primary application in imaging tumors of the liver and lymph nodes (prostate and breast cancer). An agent possessing both T1 and T2 properties would be desirable. Using such an agent would (I) provide a single drug for all applications, and simplify the inventory of the pharmacy, (ii) simplify imaging in the MRI suite, and (iii) improve patient care by permitting simultaneous examination of multiple medical problems in a single patient during a single examination, rather than requiring use of either a T1 or a T2 contrast agent.

Information regarding anatomical features within the vascular system can be obtained using contrast agents in two ways. When the contrast agent is first administered as a bolus, it initially passes through the vascular tree as a relatively coherent mass. Coordinating the time of imaging of the desired anatomical feature to the time when the bolus passes through that feature can provide useful information. This technique of contrast agent use is called first pass imaging. At a later time, the bolus has been diluted by mixing, and attains an equilibrium concentration in the vascular system. Under certain circumstances, this equilibrium or steady state can offer useful information. Imaging can be performed at an early phase, within minutes after injection of the contrast agent ("first pass"), and at a later phase, from about ten minutes after injection of the contrast agent (equilibrium phase). Gadolinium agents are suited only for first pass imaging due to their ready diffusion from the vascular system into the interstitial spaces of the tissues. Previously described colloidal iron oxides are useful for the equilibrium due to their requirement for dilute administration over a prolonged time period. Colloidal iron oxides do not leak into the interstitial space but can remain in the vascular system for hours. An agent offering the opportunity to perform both first pass imaging and equilibrium imaging would be desirable.

During administration in a medical setting of a contrast agent for "first pass" imaging, the timing of imaging and passage of the "first pass" of the contrast agent may not coincide. If a useful image was not obtained, it becomes desirable to administer a second dose of contrast agent to obtain another "first pass" image. On other occasions radiologists find it useful to examine several volumes within the patient requiring a multiple dosing regimen of contrast agent in order to obtain "first pass" images at each of multiple sites of interest. With gadolinium contrast agents, this multiple administration "first pass" application is not possible because the gadolinium leaks out of the vascular space producing a fuzzy background around blood vessels of interest. Current iron oxide colloidal based contrast agents are not suitable as they are administered not as a bolus, but as a dilute solution over a long time, obviating "first pass" applications.

Diagnosis of tumor progression in cancer patients is important for characterizing the stage of the disease, and for assessing treatment. To minimize cost and discomfort to the patient, it is desirable in an MRI examination to administer a single dose of contrast agent that would allow assessment of multiple organ systems that might be affected by the disease. For instance, in primary breast cancer, it is desirable to assess tumor status in the breast and at multiple metastatic sites including the liver, spleen, bone marrow, and lymph nodes. Administration of gadolinium based contrast agents can not satisfy this requirement due to their short half life in the body, their leakage into the vascular system, and their inability to concentrate within organs of interest. Iron oxide colloid based contrast agents such as Combidex® can serve in this multiple capacity while Feridex I.V., another iron oxide colloid contrast agent, is limited to imaging the liver and the spleen.

Administration of a contrast agent in a small volume (less then 5 mL) is desirable, as small volume administration improves the resolution obtained from first pass imaging, and minimizes injection time and discomfort to the patient. Gadolinium based contrast agents are administered in volumes of about 30 mL due to constraints caused by the solubility and potency of these agents. Currently, iron oxide based contrast agents are administered as a dilute solution in a large volume (50-100 mL) over an extended period of time (30 minutes). These constraints arise from safety issues associated with the rapid and concentrated administration of iron oxide based agents. Bolus injection is desirable in that it allows first pass imaging and shortens contact time between the patient and health care provider. Further bolus injection allows the practitioner to administer the contrast agent while the subject is in the MRI apparatus during the examination, thereby optimizing efficient use of instrument imaging time. Gadolinium based agents can be administered as a bolus.

Gadolinium based contrast agents consist of a chelating molecule and the gadolinium cation. Gadolinium is a toxic element and must be excreted from the body to avoid toxicity. Colloidal iron oxides are not excreted from the body but are processed in the liver and other organs to metabolic iron, such as the iron in hemoglobin. Thus, compositions of the invention can serve as an iron supplement for patients suffering from anemia, and are especially useful for patients undergoing treatment with erythropoietin. However, of the four general types of iron oxide compounds used as MRI contrast agents and/or hematinic agents (iron sucrose, iron gluconate, iron dextran, and the iron oxides of the present invention) all but those of the presently claimed invention have serious drawbacks making them less than desirable for their intended pharmacological use.

For example, two of the oldest iron compounds administered as hematinic agents to patients suffering from acute anemia are iron gluconate and iron sucrose, examples of which include Ferrlecit® and Venofer®, respectively. These iron compounds were developed to overcome the problem of iron toxicity observed upon injection of iron salts into a subject (see C. W. Heath et al., "Quantitative Aspects of Iron Deficiency in Hypochromic Anemia," *J. Clin. Invest.* 11(6) (1932), pp. 1293-1312). Compounds such as Ferrlecit® and Venofer® were somewhat successful in reducing free iron concentrations, the substance primarily responsible for the iron toxicity observed with iron salts. They were limited in dosage amounts and rates of administration, however, because of problems associated with serious side effects such as hypotension which arose in a significant number of patients. For example, at dosages of Ferrlecit® higher than the maximum recommended dose of ~125 mg per treatment (either diluted to 100 mL and given over the course of 1 hour, or delivered undiluted as a slow intravenous injection over the course of 10 minutes) ten to thirty percent of the patients treated suffered severe nausea and vomiting, hypotension, and other side effects. See B. Bastani et al., "Incidence of Side-Effects Associated with High-Dose Ferric Gluconate in Patients with Severe Chronic Renal Failure," *Nephrol.*, 8 (2003) pp. 8-10.

Other iron compounds were then developed to overcome the limits in dosage amounts and administration rates associated with iron gluconate and iron sucrose compounds, while still maintaining low free iron concentrations to avoid iron toxicity. One such compound is iron dextran, an example of which is INFeD®. Unfortunately, although iron dextran did allow administration of larger dosages, if given slowly, a relatively high incidence of anaphylaxis was observed, including fatal reactions. For example, from 1976-1996 in the United States, 196 allergic/anaphylactic reactions were reported with administration of iron dextran, and of those 196 cases, 31 were fatal—an unacceptable fatality rate of 15.8% of all allergic reactions observed (see Bastani et al. at 9).

The risk of a fatal response is seen as so great that Watson Pharma, Inc., the manufacturer of INFeD®, is required by the FDA to include a "black box" warning, the highest level of warning required by the FDA, on the drug information sheet that accompanies the packaging of the drug (see Exhibit A, attached hereto). Other references show the incidence of side effects for INFeD®, Dexferrum®, Ferrlecit® and Venofer® (e.g. see Exhibit B, attached hereto—"The Drug Monitor, Parenteral Iron (IV) Supplementation, by Nasr Anaizi, Ph.D.). All exhibit side effects in a relatively high percentage of patients treated, from hypotension (which is sometimes severe), nausea, and diarrhea, to chills, headache, and fever, among others.

In addition, dextran alone can also sometimes elicit a fatal anaphylactic response when administered intravenously (i.v.) in man (Briseid, G. et al., *Acta Pharmcol. et Toxicol.*, 1980, 47:119-126; Hedin, H. et al., *Int. Arch. Allergy and Immunol.*, 1997:113:358-359).

For compounds such as Ferrlecit® and Venofer®, and to a lesser extent INFeD®, the presence of free iron upon in vivo administration to a human subject is undesirable for reasons other than the reported side-effects of hypotension, nausea and diarrhea. Studies have shown that in vivo free iron is undesirable because it fosters the growth of bacteria and may even lead to increased risk of death. See Collins et al., *J. Am. Soc. Nephrol.* (1997)8, pp. 190A (Abstract); Bullen, *Rev. Infect. Dis.* (1981)3, pp. 1127-1138; and Weinberg, *Microbiol. Rev.* (1984) 64, pp 65-102. In addition, Parkinnen et al., in *Nephrol. Dial. Tansplant*, 2002, 15, pp. 1827-1834 measured free iron using a bacterial growth assay where the bacteria is *S. epidermis*. This assay is based on the knowledge that *S. epidermis* (and by implication, other Gram-negative bacteria) cannot utilize transferrin-bound iron. Parkinnen et al. showed that serum samples with calculated transferrin saturation of >80% were positive for both a BDI assay and the bacterial growth assay, whereas none of the samples with calculated transferrin saturation levels of <80% were positive for the BDI assay, although a few such samples did show slow sustained growth after a considerable lag period (see Parkinnen at 1833, col. 1, third paragraph).

Iron-induced impairment of neutrophil function, leading to decreased phagocytosis has also been reported in vitro (van-Asbeck et al., *J. Immunol*. (1984) 132, pp. 851-856) and in vivo in patients supplemented with i.v. iron (Patruta et al., *J. Am. Soc. Nephrol*. (1998)9, pp 655-663). And lastly, infusion of ferric saccharate administered at doses regularly given for intravenous iron supplementation results in a greater than 4-fold increase in non-transferrin bound iron and also causes transient reduction of flow-mediated dilatation, indicative of endothelial dysfunction (see Rooyakkers et al, *Eur. J. Clin. Inv.* 2002, 32, pp 9-16).

Overall, these findings indicate that i.v. iron dosage regimens which may lead to transferrin oversaturation should be avoided. As such, it is an embodiment of the invention that a polyol or polyether iron oxide complex in accordance with the present invention, when administered parenterally to a patient for use as a pharmacological agent, provides both minimal detectable free iron in a subject as determined by a BDI assay or by atomic absorption spectrophotometry or by a bacterial growth assay, and minimal anaphylaxis in a patient. In another embodiment, the iron oxide polyol or polyether complexes further provide minimal dissolution of the iron complex in a human subject, determined as a function of percent transferrin saturation, and in another embodiment, the polyol or polyether iron oxide complex presents in the human subject as an immunosilent complex.

An embodiment of the invention provides a method for the synthesis of a colloid of an iron oxide associated with a water soluble polyol or polyether coating in a manner that mitigates dissociation of the coating from the iron oxide when the material is subjected to heat stress, or when administered parenterally to a patient as a pharmacological formulation.

A method that is an embodiment of the invention includes the steps of treating a polysaccharide with a reducing agent such a borohydride salt or with hydrogen in the presence of an appropriate hydrogenation catalyst such Pt or Pd to obtain the reduced polysaccharide, such that the terminal reducing sugar has been reduced to give an open chain polyhydric structure. The reduced polysaccharide may be an arabinogalactan, a starch, a cellulose, an hydroxyethyl starch (HES), an inulin or a dextran.

Moreover, it is an embodiment of the invention that a polyol or polyether, including the reduced polysaccharide described above or a polyethylene glycol, may be further functionalized prior to particle formation. Such a method further comprises mixing the polyol, reduced polysaccharide, or polyether with iron salts in an acidic solution selected from the group comprising ferric salts, ferrous salts, or a mixture of ferrous and ferric salts, cooling the solution, neutralizing the solution with a base, and recovering the coated iron oxide colloid.

In accordance with a further embodiment of the invention, the bases which may be employed are sodium hydroxide, sodium carbonate and more preferably, ammonium hydroxide, for the step of neutralizing the colloid. In one particular embodiment of the invention, the polysaccharide derivative is reduced dextran and the iron salts may be ferrous and ferric salts, which produce a superparamagnetic iron oxide colloid with a water soluble coating that does not dissociate from the iron oxide core under heat stress during terminal sterilization.

In another embodiment of the invention, only ferric salts are employed, yielding a non-superparamagnetic particle.

In another embodiment, a coated colloid may be prepared by adding a polyol or polyether to an iron oxide sol (a colloidal dispersion in a liquid), adjusting the pH to 6-8 and recovering the coated iron oxide colloid.

The iron oxide polyol or polyether colloids in accordance with the invention have substantially improved physical characteristics and manufacturability compared to previously described materials. Improved physical characteristics are evident in the ability of the colloid to withstand heat stress, as measured by subjecting the colloid to a temperature of 121° C. for 30 minutes. Colloid particles made according to the invention show less evidence of polyol or polyether dissociation under stress, remaining colloidal, and exhibiting no appreciable change in size.

An example of a colloid with an unstable polysaccharide coating includes Combidex®, which when subjected to heat stress, lost 43% of its dextran coating, and increased in particle diameter size from 21 nm to 587 nm; significant clumping of material was observed upon visual analysis. Another superparamagnetic iron oxide dextran colloid, Feridex®, prepared according to U.S. Pat. No. 4,770,183, also exhibited increased particle size, as demonstrated by the inability of the heat treated colloid to pass through a filter having a 0.8 µm pore size, after a heat treatment comprising only 30 minutes at 121° C.

An example of a colloid that provides more than minimal dissolution of the complex upon parenteral administration to a subject is iron gluconate and iron sucrose During manufacture, a process that is an embodiment of the invention typically uses one tenth or less the amount of polysaccharide compared to the amount required in previous preparations using non-reduced polysaccharide, resulting in substantial raw materials cost savings due to the improved efficiency of the process of the invention.

Variation in such factors as the nature of the polyol or polyether derivative (i.e ethers, esters, amides, amines, carboxyalkylethers) concentration, polyol or polyether concentration, or base concentration and/or Fe(III)/Fe(II) concentration can produce colloids with different magnetic susceptibilities and sizes. Changing the Fe(III)/Fe(II) ratios changes the particle size and alters the magnetic susceptibility. Higher ratios (for example, 2.0 mol/mol) tend to decrease susceptibility, whereas lower ratios (for example, less than 1.5 mol/mol) tend to increase particle size.

The process may be adjusted to yield colloids with different biological properties by changing the type of polyol or polyether and further derivatizing the particle after synthesis, such as by etherification, esterification, carboxyalkylation, amidation, or amination, for example.

The colloids that are an embodiment of the invention can be used as contrast agents for magnetic resonance imaging (MRI) or in other applications such as magnetic fractionation of cells, immunoassays, magnetically targeted drug delivery, and as therapeutic injectable iron supplements. These colloids are particularly suited to parenteral administration, because the final sterilization typically is autoclaving, a preferred method since it eliminates viability of all cellular life forms including bacterial spores, and viruses.

Previous methods for making colloids required the addition of excipients such as citrate or low molecular weight polysaccharides as stabilizers during the autoclaving process (see U.S. Pat. No. 4,827,945 and U.S. Pat. No. 5,102,652), or avoided heat stress altogether by use of filter sterilization (see U.S. Pat. No. 5,150,726). Thus, the embodiments of the present invention that are the methods for synthesizing the colloids, and the embodiments of the present invention comprising the colloid compositions, provide utilities as significantly improved MRI contrast agents, and hematinic agents that are iron supplements. The improvements provided in these agents over prior art are found in the following facts demonstrated in the examples herein: that the agents which are embodiments of the present invention are heat sterilizable by autoclaving, and are thus optimized for long-term storage at ambient temperatures; that these agents do not require the addition of excipients for maintenance of stability during the sterilization or storage processes; that the agents are non-toxic to mammals including humans; that an effective dose of the agents used for imaging is a smaller amount of material than the agents described in the art; and that the pharmacokinetics following administration are such that iterated successive doses administered after a brief interval after administration of a first dose can be used to obtain additional images during a single clinical visit and use of the imaging apparatus.

In the case of polyols such as dextran and derivatives thereof, or polyethers such as polyethylene glycol and derivatives thereof, the formulations prepared by this method are less immuno-responsive in mammals, as shown by data obtained using a rat model, and in clinical trials in human subjects. The dextran- and dextran derivative-coated iron particles enhanced imaging of the heart, lungs, kidneys, and other organs and systems in three mammalian species: rat, pig, and human. The dextran- and dextran derivative-coated iron particles can be used also as hematinic agents, to provide iron in a more efficiently absorbed format than is true of oral iron supplements, to groups of patients who are chronically iron-deprived, such as dialysis patients, cancer patients, gastroenteritis patients, and recipients of erythropoietin. ELISA assays can also verify that administration of iron oxide polyol or polyether complexes in accordance with the present invention result in minimal cross-reactivity with a rat serum a-dextran antibody, as is shown in Table 2 and FIG. 1 and described in Example 1 for a polyol iron oxide complex, indicating that such compounds present as immunosilent complexes in a subject, and thus provide minimal incidence of anaphylactic response.

The derivatized reduced dextrans can be used also as plasma extenders, which, unlike blood and blood fractions, do not have to be cross-matched immunologically, and unlike human serum albumin preparation, can be sterilized in a manner that destroys viruses, including strains of hepatitis, CMV, and HIV, spongiform encephalitis, and other infectious agents. The plasma extenders of the invention do not have to be refrigerated or stored away from light and heat, and are thus advantageous in emergency medical situations, such as treatment of shock due to loss of blood such as trauma, even in tropical climates.

Example 1 describes the method for performing the ELISA assay as relied on in FIG. 1 and Table 2.

Examples 2 and 3 describe methods for measuring free iron in a sample after administration of a polyol or polyether iron oxide complex in accordance with the present invention. The results of these measurements with a polyol iron oxide complex are shown in Tables 3, 4, and 5.

Example 4 describes a method for measuring dissolution of the complex in a subject, as a function of transferrin saturation.

Example 5 describes a method for preparing a polyol or polyether iron oxide complex in accordance with the present invention.

Examples 6 and 7 describe improved methods for parenteral administration of a polyol or polyether iron oxide complex in a subject to provide minimal detectable free iron, as measured by a bleomycin catalytic assay and minimal anaphylactic response, as indicated by cross-reactivity with a rat serum α-dextran antibody and as determined by volume of paw edema.

Examples 8 and 9, respectively, describe improved methods for formulating an iron oxide complex with a polyol or polyether wherein upon administration at a delivery rate from to a subject the complex exhibits minimal dissolution in the subject, measured as a function of transferrin saturation in vivo, or whereupon administration to a subject, the complex is immunosilent in the human subject.

Examples 10, 11 and 12 show the methods for making reduced dextrans of type T1, T5, and T10, respectively. Example 13 describes preparation of reduced pullulan.

Examples 14-18 describe the synthesis of carboxymethyl reduced dextran T10 with varying degrees of carboxymethylation, from native dextran T10 (Table 6).

Examples 19-24 describe the synthesis of carboxymethyl reduced dextran T10 with varying degrees of carboxymethylation, starting with reduced dextran T10 (Table 7). Examples 25-25 describe the synthesis of carboxymethyl dextran T10, T40, and T70 from native dextran.

Examples 28-35 describe the preparation of reduced and native dextran coated iron oxides. The conditions of the reactions in these examples were chosen to yield USPIOs coated either with reduced or non-reduced polysaccharides. The reactions conditions for the native dextran iron oxide preparations were the same as for the reduced dextran preparations of the same molecular weights, to allow comparison of the effectiveness of the respective dextrans in coating particles. Mean volume diameter (MVD) and magnetic susceptibility of iron oxide preparations obtained using reduced in comparison to native polysaccharides (prepared in these examples) are summarized in Table 8.

Examples 35, 38, and 40 and 37, 29, and 41 describe procedures for the preparation of USPIOs with native T1, T5, and T10 dextrans or with PEG4000, PEG8000 or PEG10000, respectively, to obtain iron oxide colloids having a particle diameter of less than 30 nm. A comparison of effects of native dextrans (Examples 36-40) and their respective reduced dextrans (Examples 28, 30, and 32) in the synthesis and properties of iron oxide colloids is shown in Table 9.

Examples 42-43 describe the preparation USPIOs coated with carboxymethyl native dextran T10 and carboxymethyl reduced dextran T10.

Examples 44-53 describe the preparation of USPIOs coated with carboxymethyl reduced dextran T10 preparations containing varying extents of carboxymethylation. The effect of extent of carboxymethylation of CMRDs on colloid size of USPIOs is shown in Table 10. The effect of extent of carboxymethylation of CMRDs on solubility of ferric/ferrous chloride solutions is shown in Table 11.

Examples 54-60 describe the synthesis of iron oxide sols and their stabilization with native and reduced dextrans and CMRD. Example 61 describes preparation of CMRD coated non-magnetic iron oxide colloid using base precipitation of ferric chloride and CMRD.

Example 62 examines the effect of the process of sterilization by autoclaving of various preparations of USPIOs coated with reduced and native dextrans on the properties of these particles. The results are shown in Tables 12 and 13.

Example 63 reports the relaxation properties of various contrast agents comparing these properties for gadolinium based contrast agents and USPIOs prepared with native dextran and carboxymethyl reduced dextran T10 (Table 14).

In Examples 64-67, the presence of symptoms of toxicity to rats of reduced and non-reduced (native) dextran coated USPIOs was determined, with response to an anaphylactic type reaction. The extent of the anaphylactic type reaction is determined by volume of paw edema. Similar studies were performed using native, reduced, and carboxymethylated reduced dextrans. The results are summarized Tables 15-18.

Examples 65 and 66 describe a rat paw volume edema test and guinea pig anaphylaxis test, used to determine the likelihood of anaphylactic response to parenteral administration of polyol or polyether iron oxide complexes in a human subject.

Example 67 describes toxicity studies in rates of reduced and non-reduced dextran.

Figure 5:
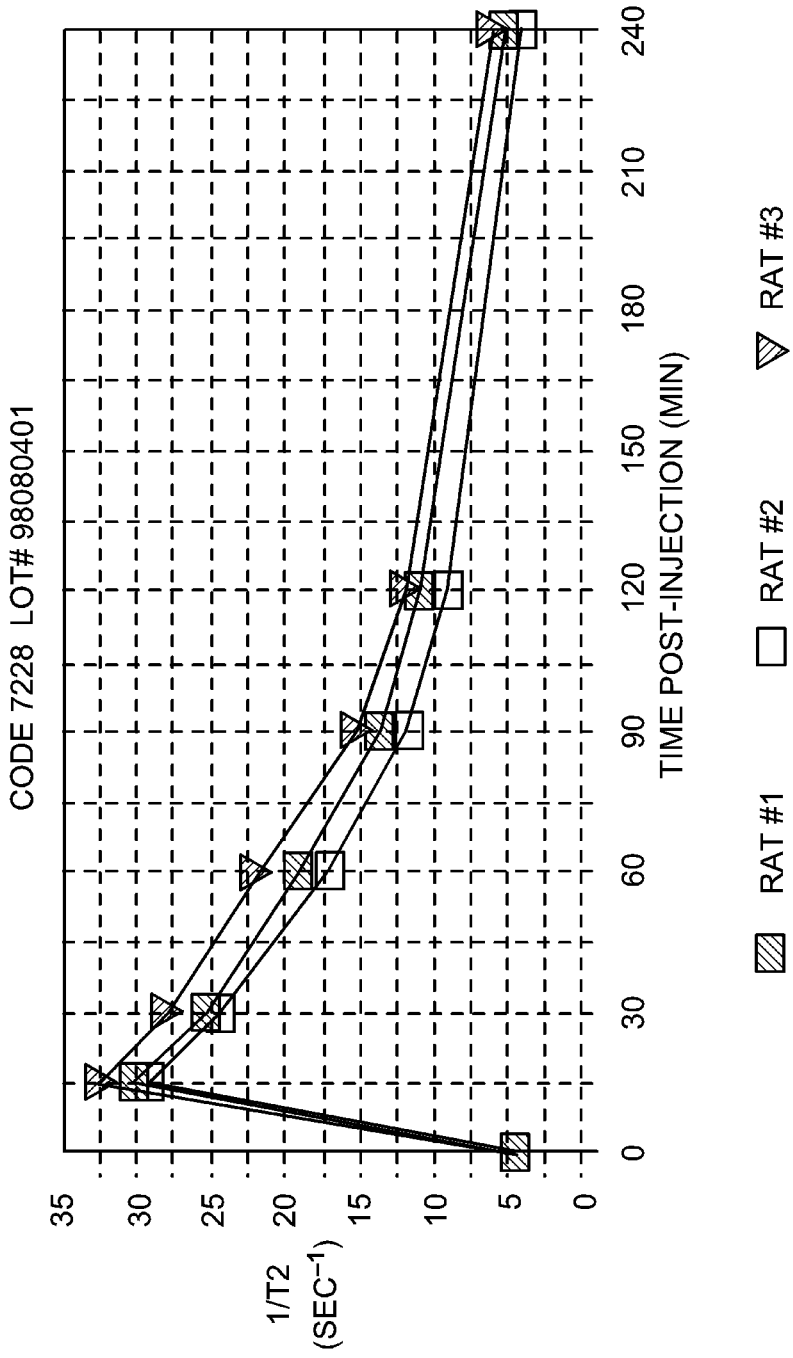
FIG. 5 shows pharmacokinetics of CMRD coated USPIO in the blood of three male rats following intravenous administration of 2.2 mg of iron per kg body weight. Samples (0.25 mL) of blood were collected at the times indicated on the abcissa, and relaxation times were measured on a Brucker Minispec spectrometer.
Figure 6:
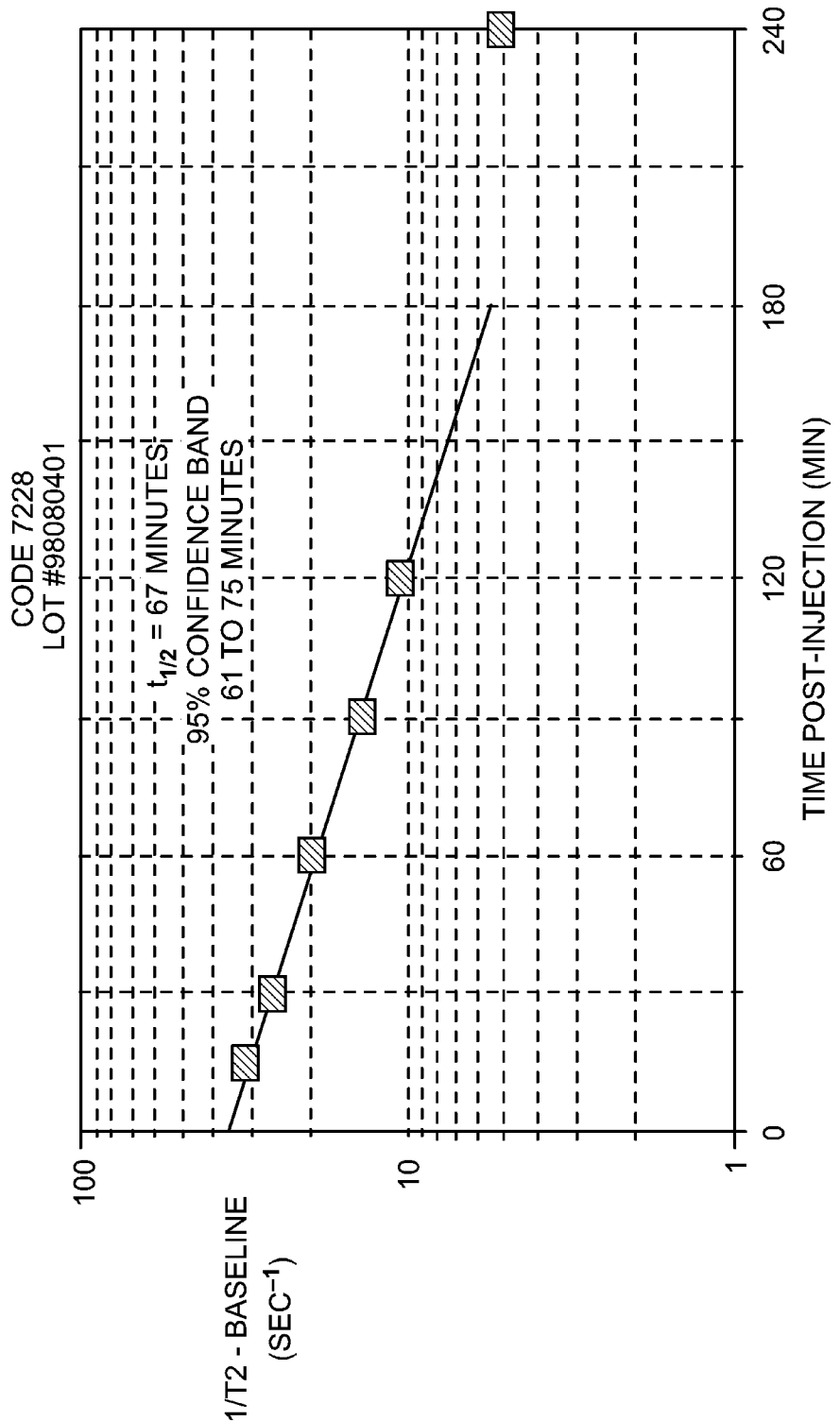
FIG. 6 shows the graph used to determine a half-life (67 minutes) of CMRD coated USPIO in rat blood. The data of FIG. 5 were used to generate the graph in FIG. 6. The half-life range of 61 to 75 minutes was within the 95% confidence level.

Example 68 and FIGS. 5 and 6 show the kinetics of clearance of a CMRD coated USPIO from rat circulation. The half-life of the agent is determined.

Figure 7A:
FIG. 7 shows MRIs of a rat, pre-administration (A) and post-administration (B) of contrast agents, anterior portion at top. CMRD coated USPIO (5 mg of iron per kg body weight) was administered into the femoral vein prior to taking the post administration contrast image. The figure illustrates enhanced visualization of the heart and surrounding arteries and veins caused by administration of CMRD coated USPIO. Imaging was performed using a General Electric 2 Tesla magnetic resonance imager.

An enhanced MRI scan is shown in Example 69 and FIG. 7 following administration of CMRD coated USPIO, the scan showing images of the rat heart, aorta and other cardiac-associated arteries. Example 70 and FIG. 8 show a CMRD coated USPIO enhanced MRI scan of the anterior portion of a pig. Example 71 shows that injection of CMRD coated USPIOs into human subjects, as part of a clinical trial, produced no adverse effects. Example 72 describes the biodistribution (FIG. 9), imaging kinetics (FIG. 10 and Table 19), and absence of background in MRI usage of this material in humans. The data in this example show the ability of the practitioner of the invention to perform multiple administrations and obtain subsequent images within the real time of an office visit or visit to a MRI facility.

EXAMPLES

Example 1

ELISA Assay

Plastic microplates were pre-coated with a dextran-BSA conjugate. To each microwell was added 100 microliters of IV—Fe at serial dilution concentrations, followed by 100 microliters rat serum containing antibodies against dextran. The plate was incubated for 1 hour at room temperature, decanted and washed with 0.2% Tween 80 solution in water. To each well was added 200 microliters of anti-rat IgG-alkaline phosphatase conjugate. The plate was incubated for 1 hour at room temperature, decanted and washed with 0.2% Tween 80 solution in water. To each well was added 200 microliters of p-nitrophenylphosphate. The plate was incubated at room temperature for 8 minutes, and the absorbance of the wells was read at 405 nm. Samples of dextran T70 and the IV—Fe were run at the same time. ED50 values were calculated using the Molecular Devices Microplate reader software.

Significantly, C-7228, when administered parenterally to a subject, provides minimal anaphylaxis. Using an ELISA assay to measure cross-reactivity of intravenous iron versus dextran as the method for determining anaphylactic response, it was observed that at 730 mg Fe/mL for compound 7228 only 11% cross-reactivity was detected, compared to 467% cross-reactivity for InFeD® at only 15 mg Fe/mL (Table 2 and accompanying FIG. 1).

As can be seen in Table 2 and FIG. 1, C-7228, even at levels of 730 μg of Fe/mL dosage resulted in only 11% cross-reactivity, whereas INFeD® at only 15 μg Fe/mL resulted in 467% cross-reactivity. At comparable levels of C-7228 to those of INFeD® (i.e. C-7228 at 15 μg Fe/mL) cross-reactivity with C-7228 was undetectable.

TABLE 2

ELISA data showing levels of cross-reactivity with rat serum α-dextran antibodies for C-7228 compared to InFeD ®.

| ELISA | — | — | — |
|---|---|---|---|
| Dextran T10 Coated Plate | — | — | — |
| Rat Serum α-Dextran Antibody | — | — | — |
| — | — | — | — |

| Inhibitor | ED50 ug Fe/mL | T70 ED50 ug/mL | cross reactivity |
|---|---|---|---|
| — | — | — | — |
| 7228 | 730 | 77 | 11% |
| INFeD ® | 15 | 70 | 467% |

Example 2

Free Ionic Iron Determined by Atomic Absorption

Atomic absorption (AA) spectrophotometry is used to determine free ionic iron in samples filtered through a 30-K molecular weight cut-off micropartition membrane.

Materials
  AA Spectrophotometer (Perkin Elmer 3100 or equivalent) wavelength 296.7 nm, equipped with iron lamp and air/acetylene flame.
  5 ppm, 10 ppm, 15 ppm and 20 ppm Iron standards (NIST traceable)
  Pipets/tips
  Purified water
  Centricon 30-K membrane filters—AMI Code 1582
  Tabletop centrifuge with fixed angle rotor capable of 1000-5000×g Standard Preparation
  Working standards are prepared according to the following dilutions shown in Table 3.

TABLE 3

| Standard Concentration | Amount of 1000 ppm Standard per Liter |
|---|---|
| 5 ppm | 5 mL |
| 10 ppm | 10 mL |
| 15 ppm | 15 mL |
| 20 ppm | 20 mL |

Sample Preparation
  Each sample is mixed by preparing an accurate 1:10 volumetric dilution of each sample in purified water in a microconcentrator tube by pipetting 200 μL of the sample into the tube and adding 1.8 mL of water. For each dilution, the sample is dispersed with a pipet tip and the dilution factor ($D_i$=10) is recorded.

Filled Amicon tubes are centrifuged at 1000×g at room temperature for 30 minutes with care taken to not exceed the recommended centrifuge speed for Centricon 30-K membrane filters. Each eluent is then diluted 1:2 with purified water in a test tube to obtain sufficient volume for AA determination. The second dilution is then recorded on the data sheet as $D_e$ and each sample dilution is then mixed before reading an AA.

Assay
  The atomic absorption spectrophotometer is set up according to the particular instrument instructions. In the case of a Perkin-Elmer 3100 spectrophotometer, the instrument has a single element iron hollow cathode lamp, an oxidizing lean, blue air-acetylene flame, a flow spoiler, and a stainless steel nebulizer. The instrument settings are then: spectral line, 296.7 nm; slit width, 0.2 nm; integration time, 1.0 seconds; and readings per sample, 10. The instrument is used with a background correction enabled, if available, with the results calculated in ppm by the instrument.

The instrument is first calibrated using zero (purified water) and 20 ppm standards. Continue calibrating the instrument with controls of 5, 10 and 15 ppm which are measured and read. Results must be within specified ranges. Once the AA spectrophotometer is properly calibrated, the iron concentration for each test sample solution is measured. The sampling tube is rinsed with purified water between each sample, which acts to reset the automatic zero on the instrument.

Calculations
  For AA readings of 1.0 ppm or less, the final value is reported as "less than" the calculated concentration of 1 ppm reading (P=1 in the formula below). The ionic iron content in mg/mL is then calculated using the following formula:

$$\frac{mg}{mL} = \frac{P \times D_i \times D_e}{1000 \; \mu g/mg}$$

where $P$ = Value from $AA$ $(ppm)(\mu g/mL)$ $D_i$ = Initial sample dilution factor ( = 10)

$D_e$ = Eluent dilution factor ( = 2)

Using this formula, the final value is then less than 0.02 mg/g for AA readings of 1.0 ppm or less.

The percent ionic iron, as mg/mL obtained in this assay divided by the total iron concentration of the original sample, can then be calculated. For AA readings of 1.0 ppm or less, the value is reported as <0.1%. As shown in Table 4, results from quality control tests done on an iron complex in accordance with the present invention—Code 7228 (C-7228)—are compared to the results of the same tests done on Ferrlecit® (iron gluconate), Venefer® (iron sucrose), InFeD® (iron dextran), and Dexferrum® (iron dextran). As can be readily seen, compound 7228 produces only 0.001% free iron in solution (when measured using atomic absorption spectrophotometry on samples filtered through a 30-K filter molecular weight cut-off micropartition membrane filter) as compared to 2.36% for Ferrlecit®, 0.038% for Venofer®, 0.29% for InFeD®, and 0.000% for Dexferrum®. In another measurement to show free iron, listed as iron dialyzed % in the R&D tests, C-7228 shows 0% compared to 3.7% and 1.8% for Ferrlecit® and Venofer®, respectively. C-7228 also contains zero particulates≧10μ and just one particulate≧25μ, compared to 6≧10μ and 7≧25μ for Ferrlecit®, for example.

TABLE 4

Tests Comparing C-7228 to Other Iron Oxide Complexes Currently Available

| | C-7228 | Ferrlecit ® | Venofer ® | INFeD ® | Dexferrum ® |
|---|---|---|---|---|---|
| Free iron (30K Filter | 0.001% | 2.360% | 0.038% | 0.298% | 0.000% |
| Iron dialyzed % (corrected for control) | 0% | 3.7% | 1.8% | 0% | 0% |

TABLE 5

Catalytic Bleomycin Assay showing Bleomycin Detectable Iron (BDI) for solution of known iron oxide complexes Ferrlecit ®, Venofer ®, and INFeD ® compared to C-7228

| | Total Fe | | Catalytic Fe (BDI) | | |
|---|---|---|---|---|---|
| I.V.-Fe | μM | μg/mL | μM | μg/mL | % of dose |
| Ferrlecit ® | 578 | 32.3 | 8.19 | 0.457 | 1.42% |
| Venofer ® | 610 | 34.1 | 4.3 | 0.240 | 0.70% |
| INFeD ® | 574 | 32.1 | 1.18 | 0.066 | 0.21% |
| C-7228 | 566 | 31.6 | 0.48 | 0.027 | 0.08% |

Example 3

Free Iron Determined by a Bleomycin Detectable Iron (BDI) Assay

Another sensitive assay for determining free iron concentration is a catalytic bleomycin assay referred to as the BDI assay. This standard assay uses the anti-tumor compound bleomycin, which requires catalytic amounts of iron for activity, to detect the presence of iron in a solution, with the ability to detect free iron concentrations below 50 nm (see FIG. 2 and throughout in M. J. Burkitt et al., *Clin. Sci.* (2001) 100, pp. 238-247 hereby incorporated by reference herein).

There are two common versions of the BDI assay, one utilizing changes in ethidium bromide-enhanced fluorescence of DNA to determine free iron concentrations, (see Burkitt, supra) and the other utilizing measurement of DNA damage through formation of malondialdehyde (MDA), which then forms a chromophore with thiobarbituric acid (TBA) known as the $(TBA)_2$-MDA adduct which can be measured by ultraviolet spectroscopy at 532 nm (see J. M. Gutteridge et al. (1987) *Life Chem. Rep.* 4, 113-142 and P. J. Evans et al., (1994) *Methods Enzymol.* 233, 82-92 both of which are hereby incorporated by reference herein).

Table 5 shows the results of a BDI assay done to measure intravenous (I.V.) free iron concentrations in solutions of Ferrlecit®, Venofer®, and INFeD® as compared to C-7228. As can be seen below in Table 5, total iron administered for the different iron complexes ranged from 578 to 610 μM, or 32.3 to 34.1 μg/mL, depending on the units reported. However, bleomycin-detectable iron (BDI) was lowest for C-7228 and highest for Ferrlecit®, whether reported as μM, μg/mL, or % of dose delivered.

Example 4

Determination of the Dissolution of C-7228 and Other Polyol or Polyether Iron Oxide Complexes as a Function of Transferrin Saturation In Vivo Transient measurements of transferrin "oversaturation" (i.e. greater than 100% saturation) have been reported after intravenous treatment with iron gluconate (such as Ferrlecit®) and iron sucrose (such as Venofer®), see Kooistra et al., *Eur. J. Clin. Invest.* (2002) 32 (Suppl. 1) pp. 36-41, which is hereby incorporated by reference herein. Such measurements are indicative of iron oxide complexes that effectively fall apart in vivo. Compounds in accordance with the present invention show minimal dissolution after i.v. treatment in subjects, as indicated by transferrin saturation. In accordance with embodiments of the present invention, iron oxide complex dissolution is determined as a function of transferrin saturation, or oversaturation. Procedures for measuring % transferrin saturation are well-known in the art, and are described in Singh et al., *Anal. Biochem.* (1990) 186, pp. 320-323; Kooistra et al., *Eur. J. Clin. Inv.* (2002) 32, pp. 36-41; and Parkinnen et al., *Nephrol. Dial. Transplant* (2000) 15, pp. 1827-1834 at pp. 1829-1830, the entire contents of which are all hereby incorporated by reference herein. In addition, using a procedure outlined in Kooistra et al. (see above), the concentration of total plasma iron binding sites can be determined using a calculation based on serum transferrin concentration.

Transferrin iron binding capacity is calculated as follows (using the molecular weight of transferrin to be 79.57 kD and 1 mol of transferrin equals 2 mol of iron binding sites):

Transferrin iron binding capacity (μmol/L)=serum transferrin (g/L)×25.14

Thus, when all iron binding sites in plasma derive from transferrin molecules, $$\text{Transferrin saturation} = \frac{\text{serum iron (μmol/L)}}{\text{transferrin iron binding capacity (μmol/L)}}$$

Therefore, it is possible to determine whether an iron oxide complex undergoes dissolution upon i.v. administration by determining the % transferrin saturation. In particular, a % transferrin saturation of over 100% (oversaturation) is strongly indicative of a complex that undergoes rapid and extensive dissolution in vivo.

Example 5

Preparation of Carboxyalkyl Polyether Compounds

The following solutions are prepared and cooled to 5° C.: Solution A: 10.5 N sodium hydroxide in water; Solution B: 4.34 M haloalkylcarboxylic acid; and Solution C, 75.7 g of polyether ethylene glycol in 187.5 mL water.

Solution A (150 mL) was added to Solution C all at once. After 5 min, 145 mL of Solution B is added and the combined solution is then stirred for 120 min while the temperature is maintained between 20° C. and 25° C. The mixture is neutralized with 6 M HCl, passed through a 0.2-μm pore size filter, and diluted to 2 liters. The product is purified by repeated ultrafiltration against a 3-kDa MWCO ultrafiltration membrane, 0.2 μm filtered again, and lyophilized. The yield is then determined and the recovered solid carboxyalkyl ether of ethylene glycol (sodium salt) is titrated to determine the carboxyl content per gram of product.

The concentrations of Solution A, Solution B and Solution C can be varied and optimized, with the above concentrations as guidelines, to achieve the desired level of carboxyalkylation of the ethylene glycol product. For example, varying amounts (~100 mL to 300 mL) of ~8 N to 12 N sodium hydroxide solutions can be used for Solution A, while the amounts (~125 mL to 200 mL) and concentration (~2.75 M to 3.75 M) of Solution B may also vary as needed, according to amount and concentration of starting polyether compound.

Example 6

Improved Method of Administering a Derivatized Polyol or Polyether Iron Oxide Complex in a Subject to Provide Minimal Detectable Free Iron Iron oxide polyol or polyether complexes such as carboxyalkyl-. amino-, amido-, or ester derivatives of reduced dextran iron oxide complexes, or carboxyalkyl-, amino-, amido- or ester derivatives of ethylene glycol iron oxide complexes in accordance with the present invention are administered parenterally by bolus injection at a dosage of from about 1 mg to about 4 mg of iron/kg of body weight, administered all at once in a 5-mL, 10-mL or up to 15-mL saline solution, wherein administration of the complex results in minimal detectable free iron, as measured either by atomic absorption spectroscopy as described in Example 2, or as measured by a BDI assay as described in Example 3 and the references therein.

Example 7

Improved Method of Administering a Polyol or Polyether Iron Oxide Complex in a Subject to Provide Minimal Anaphylactic Response Iron oxide polyol or polyether complexes such as carboxyalkyl-. amino-, amido-, or ester derivatives of reduced dextran iron oxide complexes, or carboxyalkyl-, amino-, amido- or ester derivatives of ethylene glycol iron oxide complexes in accordance with the present invention are administered parenterally by bolus injection at a dosage of from about 1 mg to about 4 mg of iron/kg of body weight, administered all at once in a 5-mL, 10-mL or up to 15-mL saline solution, wherein administration of the complex results in minimal anaphylactic response, as measured either by an ELISA assay as described in Example 1, or as indicated by volume of rat paw edema as described in Example 65 and the references therein.

Example 8

Improved Method for Formulating an Iron Oxide Complex with a Polyol or Polyether Having Minimal Dissolution In Vivo A polyol or polyether iron oxide complex in accordance with the present invention is formulated for parenteral administration and supplied in a sterile biocompatible liquid solution, preferably sterilized by autoclaving and/or microfiltration with a 0.2-μm filter, at a concentration of 50, 75, or 100 mg/mL in 1-mL to 5 mL single dose vials for intramuscular or intravenous injection. Each mL contains approximately 0.9% saline solution (sodium chloride) in water, and sodium hydroxide and/or hydrochloric acid may have been used to adjust the pH to between about 5.2 and 6.5. The formulations of the present invention are prepared such that upon administration to a patient the iron oxide complex remains intact in vivo and displays minimal dissolution, as measured by % transferrin saturation, a BDI assay, and/or a bacterial growth assay.

In other methods for administration, the iron oxide is administered as a bolus injection wherein the iron oxide is dissolved in a biocompatible liquid as above, and injected all at once in a high concentration/low volume injection. Such injection means a concentration of iron oxide in the biocompatible liquid at concentrations of between about 50 mg/mL to about 200 mg/mL, in total volumes from between about 1 mL to about 5 mL.

Example 9

Improved Method for Formulating an Iron Oxide Complex with a Polyol or Polyether that is Immunosilent in a Human Subject A polyol or polyether iron oxide complex in accordance with the present invention is formulated for parenteral administration and supplied in a sterile solution, preferably sterilized by autoclaving and/or microfiltration with a 0.2 μm filter, at a concentration of about 50, 75, 100 or 200 mg/mL in about 1-mL to 5-mL single dose vials for intramuscular or intravenous injection. Each mL contains approximately 0.9% saline solution (sodium chloride) in water, and sodium hydroxide and/or hydrochloric acid may have been used to adjust the pH to between about 5.2 and 6.5. The formulations of the present invention are prepared such that upon administration to a patient the iron oxide complex presents as an immunosilent agent to the patient, as indicated by the patient's physical response and confirmed by ELISA assay.

General Procedures for the Synthesis of Reduced Polysaccharides

Reduced polysaccharides were prepared by treatment with excess sodium borohydride and generally purified using five cycles of ultrafiltration. Distilled water is used throughout the examples. In the case of the polysaccharide pullulan, the reduction mixture was used without further purification. In all cases, the products showed less than 5% residual aldehyde content. Residual aldehyde concentration was determined using a modified tetrazolium blue assay (Jue, C. K. et al., *J. Biochem. Biophys. Methods*, 1985, 11:109-15). Dextran concentration was determined by a phenol/sulfuric acid assay (Kitchen, R., *Proc. Sugar Process. Res. Conf,* 1983, 232-47). In cases where ultrafiltration was omitted, it was demonstrated that, except for the dextran T1, the residual borate salts did not affect particle formation. Examples 10 through 13 provide methods of synthesis of reduce polysaccharides T1, T5, and T10 dextrans, and pullulan, respectively. Retention times were determined using a Waters Ultrahydrogel 250 column, SN T52262A33, with 20 mM phosphate buffered saline, 0.4 mL/min flow rate.

Example 10

Reduced Dextran T1

Dextran T1 (10 g) was dissolved in 100 mL water at 25° C., 1.0 g of sodium borohydride was added, and the mixture was stirred for 12 h. The pH was brought to 5.0 using 6 M HCl, and 200 mL ethanol (anhydrous) was added. The precipitate was collected by centrifugation. The ethanol/water layer was decanted, and the residue was dissolved in 100 mL water. Addition of 200 mL of absolute ethanol was used to cause a second precipitation, and the ethanol/water was again decanted. The precipitated product was dissolved in water, and was lyophilized to produce a white solid, with a 60% yield. The observed HPLC retention times (min) were: for reduced dextran, 24.4; and for native dextran, 24.4.

Example 11

Reduced Dextran T5

Dextran T5 (4 g) was dissolved in 25 mL water at 25° C., 83 mg of sodium borohydride was added, and the mixture was stirred for 12 h. The pH was brought to 5.0 using 6 M HCl. The mixture was ultrafiltered against a 1 kDa molecular weight cut-off (MWCO) membrane filter. The product was lyophilized to produce a white solid, and a 70% yield was obtained. The observed HPLC retention times (min) were: for reduced dextran, 22.9; for native dextran, 21.9.

Example 12

Reduced Dextran T10

Dextran T10 (5,003 g) was dissolved in 26,011 g water. Sodium borohydride was added (52.5 g) and the mixture was stirred for 24 hours. The pH was adjusted to 7.1 using 6 N HCl. The product was purified by repeated ultrafiltration against a 3 kDa ultrafiltration membrane and lyophilized to produce a white solid. Yield: 3129 g. The observed HPLC retention times (min) were: for reduced dextran, 21.6; for native dextran, 21.1.

Example 13

Reduced Pullulan

Pullulan (90 mg) was dissolved in 0.8 mL water at 25° C., and 1 mg of sodium borohydride was added. The mixture was stirred for 12 h, and was used directly in the preparation of USPIO.

General Procedures for Synthesis of a Carboxymethyl Reduced Dextran Using Native Dextran T-10 as a Substrate.

Examples 14-18 describe the synthesis of carboxymethyl reduced dextrans from native dextran. Two general methods of synthesis are presented, a low dextran concentration method (Example 145) in which the starting concentration of native dextran was 70 mg/g, and a high dextran concentration method (Examples 15-18), in which the starting concentration of native dextran was 240 mg/g.

Example 14

Carboxymethyl Reduced Dextran T10 Prepared by the Low Dextran Concentration Method The following solutions were prepared and cooled to 5° C.: Solution A contained 4,200 g sodium hydroxide in 10.5 liters of water; and Solution B contained 2,310 g bromoacetic acid in 5,700 mL water. Solution C contained 3,000 g dextran T10 in 7,500 mL water, heated to 38° C.

Sodium hydroxide (600 g) was dissolved in 7.5 liters of water and was warmed to 38° C. Sodium borohydride (60 g) was added and the mixture was stirred for 2 min before adding Solution C, followed immediately by adding a second 60 g portion of sodium borohydride. The mixture was stirred at 38° C. for 30 min, and then cooled to 15° C. Solution A was added, keeping the temperature of the solution below 25° C. Solution B was added, and the temperature of the solution was maintained below 25° C. The mixture was stirred for 2 hours at room temperature, and was neutralized to pH 7.5 using 6M HCl cooled to 5° C., maintaining the solution temperature below 35° C. The mixture was filtered though a 0.2 μm filter, and diluted to 80 liters. The product was purified by repeated ultrafiltration through a 3 kDa MWCO ultrafiltration membrane, again filtered through a 0.2 μm filter and was lyophilized.

Figure 2:
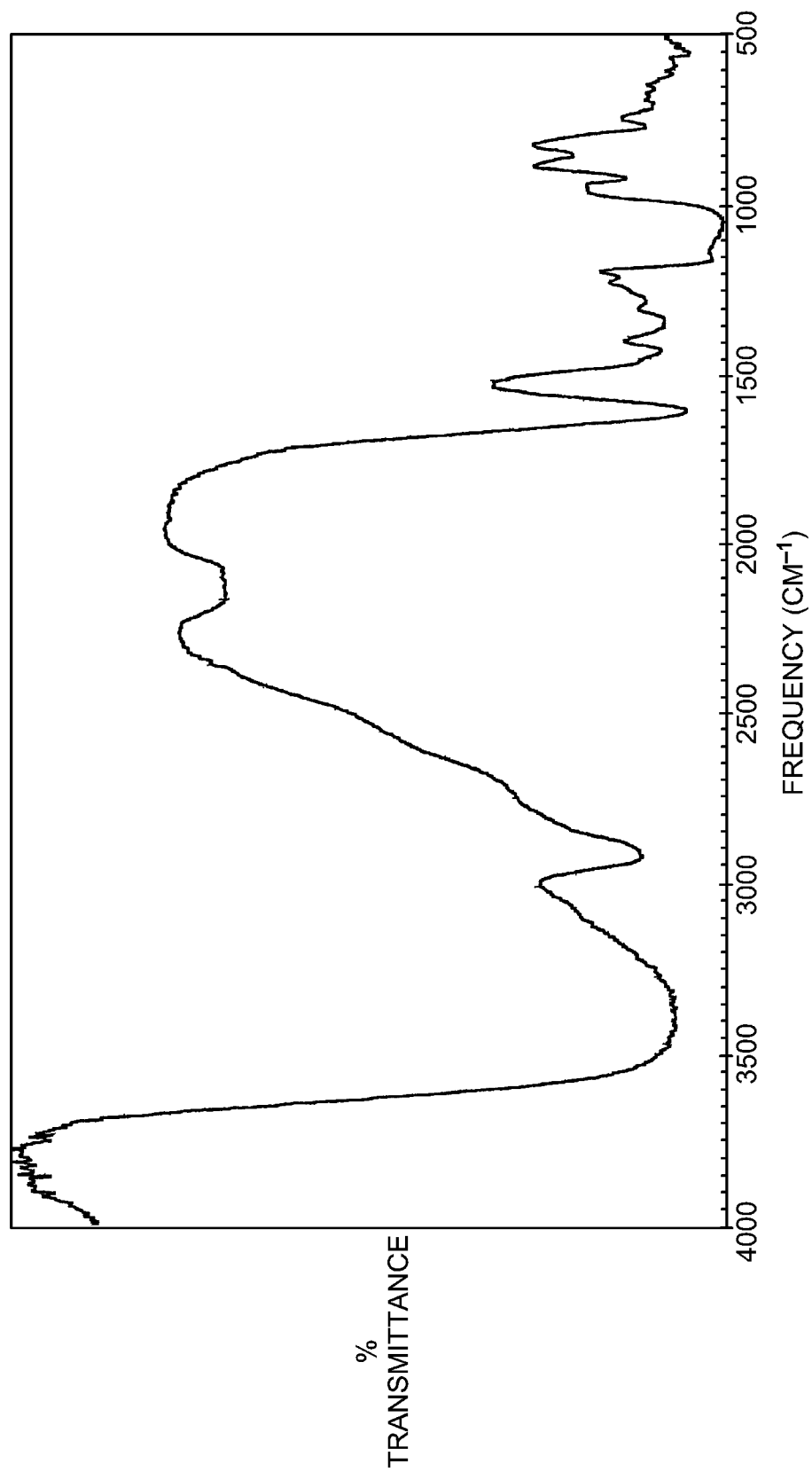
FIG. 2 shows a Fourier transform infrared (FTIR) spectrographic analysis of carboxymethyl reduced dextran (CMRD) sodium salt obtained with Example 14.
Figure 3:
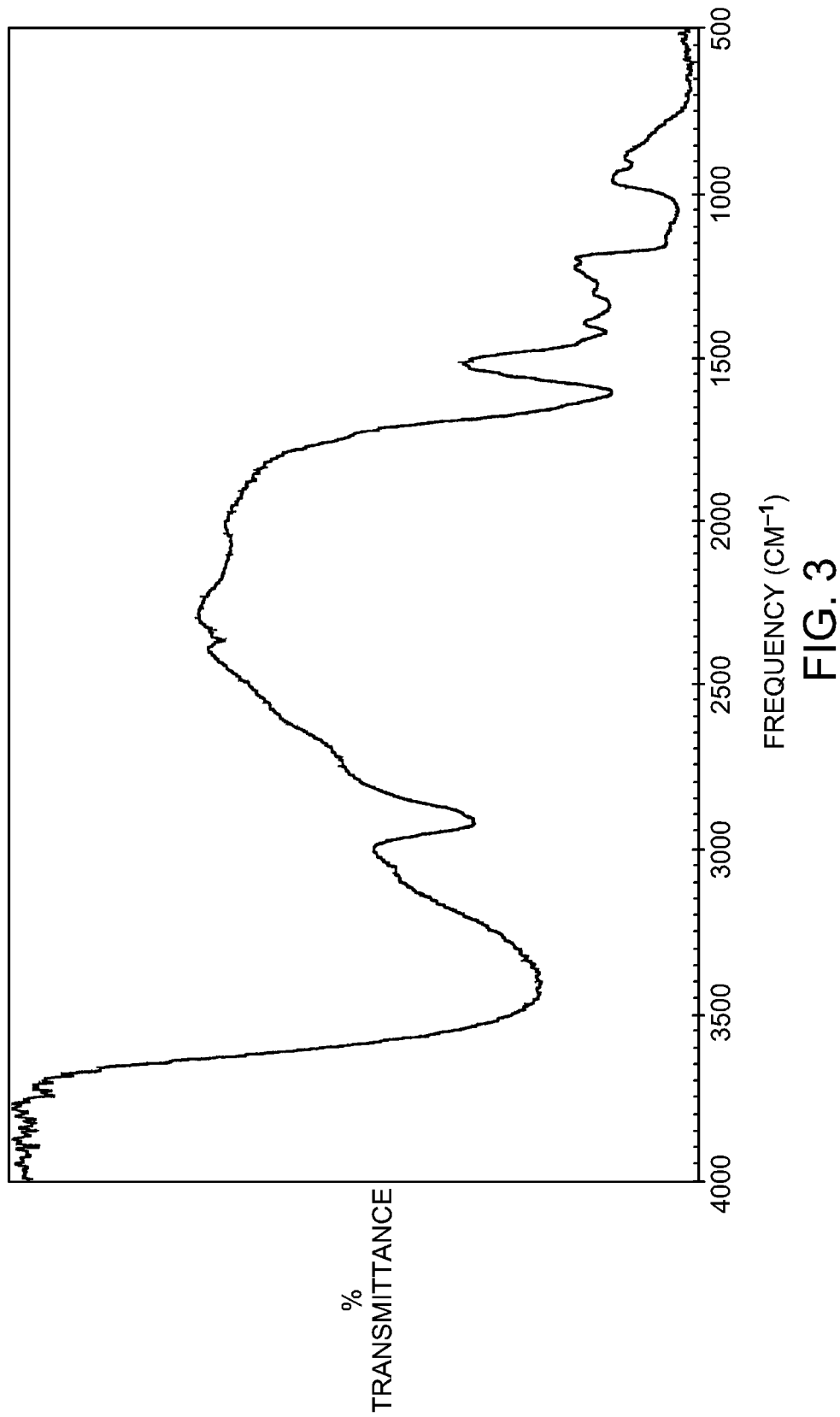
FIG. 3 shows an FTIR spectrographic analysis of sodium salt CMRD coated ultrasmall superparamagnetic iron oxide (USPIO; see U.S. Pat. No. 5,055,288) obtained in Example 43.

The recovered solid, 2,560 g of carboxymethyl reduced dextran T10 (sodium salt), showed a carboxyl content of approximately 1,265 micromoles carboxyl per gram of product, as determined by titration. The use of bromoacetic acid allowed the reaction to proceed at a lower temperature compared to use of chloroacetic acid, and produced a cleaner product as evidenced by its FTIR spectrum (FIG. 2). FIG. 2 shows no carbonyl absorption other than that of the carboxylate at 1600 $cm^{-1}$, unlike the FTIR of the product in U.S. Pat. No. 5,204,457 which was prepared with chloroacetic acid.

Example 15

Carboxymethyl Reduced Dextran CMRD T10 Prepared by the High Dextran Concentration Method Sodium borohydride (0.4 g) and 0.5 g of a 50% solution weight/weight of sodium hydroxide in water were added to a solution of 25 g dextran in 50 g water. The mixture was stirred 4 hours at room temperature, 19.5 g of the 1:1 sodium hydroxide solution and 6.2 g bromoacetic acid were added, and the temperature was kept below 25° C. using an ice bath. The mixture was then stirred 16 hours at room temperature.

To purify the product, the pH of the mixture was adjusted to pH 6.2 using 6 M HCl, and 120 mL ethanol was added. A precipitate formed and was allowed to settle, and the supernatant was removed by decanting. The residue was dissolved in 60 mL water, and 200 mg sodium chloride was added, followed by 30 mL ethanol, and the carboxymethyl reduced dextran was allowed to settle out. The sequence of addition of water and sodium chloride followed by dissolution of the precipitate and ethanol precipitation, was repeated an additional two times. The residue was dissolved in 60 mL water, and 1 liter of ethanol was added. The carboxymethyl reduced dextran was again allowed to settle out, and the solid was collected on a medium frit glass filter. The white solid was dried 24 hours at 50° C. The yield was 27 g of product having 1108 micromoles carboxyl per gram as measured by titration (Table 6).

Example 16

Carboxymethyl Reduced Dextran T10 Prepared by the High Dextran Concentration Method Sodium borohydride (0.4 g) and 0.5 g of 50% sodium hydroxide were added to a solution of 25 g dextran in 50 g water. The mixture was stirred 4 hours at room temperature, 20.0 g 50% of sodium hydroxide and 6.95 g of bromoacetic acid were added and temperature was kept below 25° C. using an ice bath while the mixture was stirred for 16 hours at room temperature. The product was purified as described in Example 15. The yield was 23.9 g of product having 1262 micromoles carboxyl per gram as measured by titration (Table 6).

Example 17

Carboxymethyl Reduced Dextran T10 Prepared by the High Dextran Concentration Method Sodium borohydride (0.4 g) and 0.5 g of 50% sodium hydroxide were added to a solution of 25 g dextran in 50 g water. The mixture was stirred for 4 hours at room temperature, and 20.67 g of 50% sodium hydroxide and 7.65 g bromoacetic acid were added while the temperature was kept below 25° C. using an ice bath. The mixture was stirred for 16 hours at room temperature. The product was purified as described in Example 15. The yield was 24.5 g of product having 1404 micromoles carboxyl per gram as measured by titration (Table 6).

Example 18

Carboxymethyl Reduced Dextran CMRD T10 Prepared by the High Dextran Concentration Method Sodium borohydride (0.4 g) and 0.5 g of 50% solution of sodium hydroxide were added to a solution of 25 g dextran in 50 g water. The mixture was stirred for 4 hours at room temperature, and 20.67 g of 50% sodium hydroxide and 7.65 g of bromoacetic acid were added while the temperature was kept below 25° C. using an ice bath. The mixture was stirred for 16 hours at room temperature, and the product was purified as described in Example 15. The yield was 23.4 g of product having 1528 micromoles carboxyl per gram of product as measured by titration (Table 6).

Figure 4:
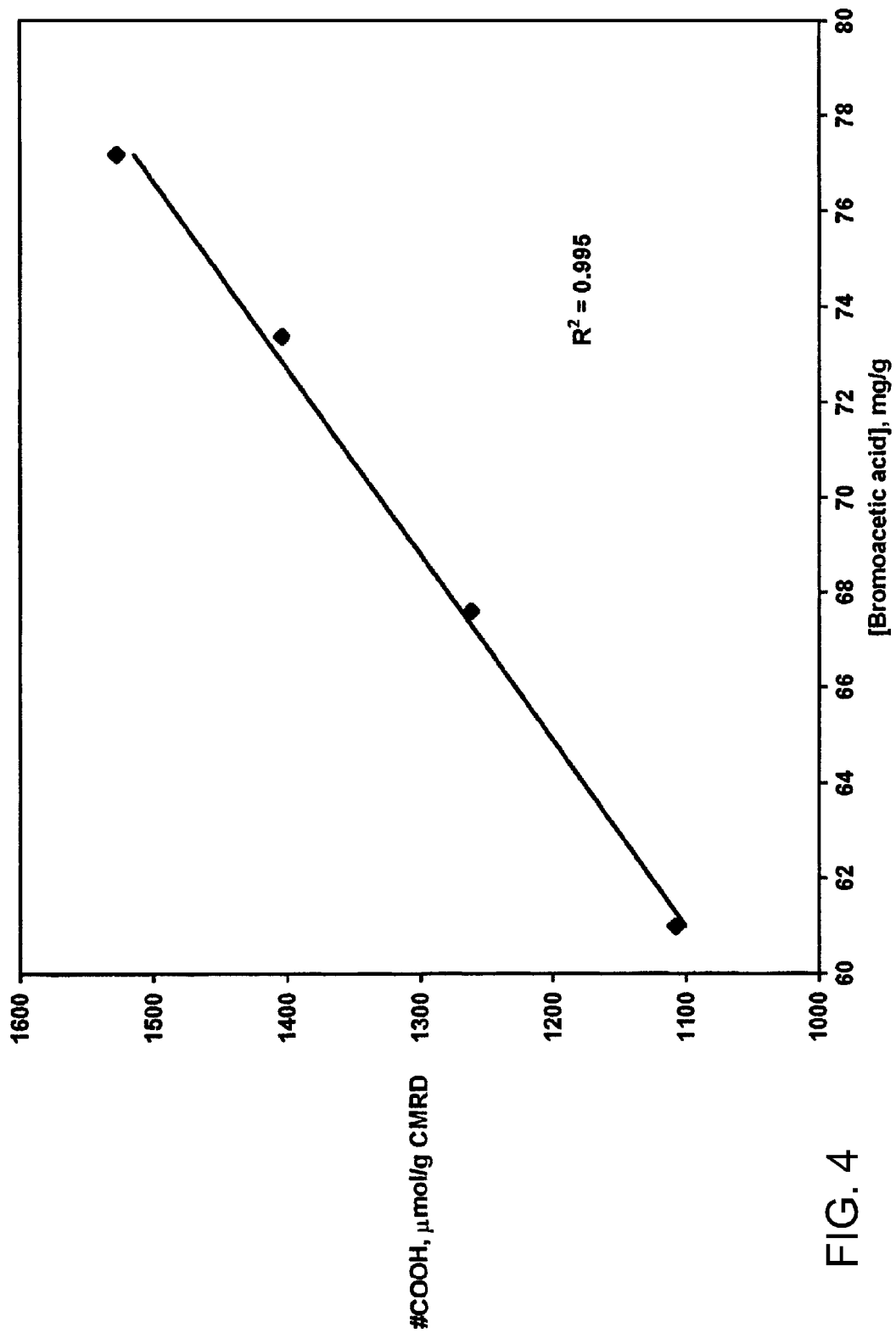
FIG. 4 is a graph that shows the amount of carboxymethyl groups (micromoles) per gram of product, on the ordinate, as a function of the amount of bromoacetic acid mg/gram used in reactions with reduced dextran starting material, on the abscissa. The graph is plotted from the data of Table 6.

The relationship between amount of bromoacetic acid used in the synthesis and the resulting incorporation of micromoles of carboxyl groups into dextran was examined using the high dextran concentration method. The relationship was found to be linear (see Table 6 and FIG. 4). Reactant masses and carboxymethyl yields for Examples 15 through 18 are shown in Table 6.

TABLE 6

Conditions for CMRD synthesis extent and degree of carboxymethylation of the product.

| Example | dextran mg/g | NaOH, mg/g | bromoacetic acid, mg/g | micromoles COOH per g product |
|---|---|---|---|---|
| 15 | 246 | 96.0 | 61.0 | 1108 |
| 16 | 243 | 97.2 | 67.6 | 1262 |
| 17 | 240 | 99.2 | 73.4 | 1404 |
| 18 | 238 | 100.3 | 77.2 | 1528 |

Synthesis of Carboxymethyl Reduced Dextran Preparations Using Reduced Dextran T-10 by the Low Dextran High Base Method Examples 19-23 describe the synthesis of carboxymethyl reduced dextrans with varying degrees of substitution starting with a low concentration of reduced dextran. In this method, the starting concentration of reduced dextran was 70 mg/g and the NaOH was at least about 107 mg/g. Table 7 shows that the extent of carboxymethyl substitution increased as the amount of bromoacetic acid used in the reaction increased.

Example 19

Carboxymethyl Reduced Dextran CMRD T10 Using the Low Dextran High Base Method

Reduced dextran T10 (15 g) was dissolved in 72 mL water, and 72 mL of 8M sodium hydroxide was added. The mixture was brought to 25° C., and a solution of 1.15 g bromoacetic acid in 3 mL of water was added. The mixture was stirred at room temperature for 1 hour, and then added to a 75 mL volume of crushed ice. The pH of the solution was brought to pH 6.0 using 6M HCl. After repeated ultrafiltration against a 3 kDa ultrafiltration membrane, the product was lyophilized. The yield was 13.25 g of product. The recovered solid, carboxymethyl reduced dextran T10 (sodium salt), showed a carboxyl content of approximately 110 micromoles carboxyl per gram as determined by titration (Table 7).

Example 20

Carboxymethyl Reduced Dextran T10 Using the Low Dextran High Base Method

Reduced dextran T10 (150 g) was dissolved in 720 mL water, and 720 mL of 8M sodium hydroxide was added. The mixture was brought to 25° C., and a solution of 11.5 g bromoacetic acid in 140 mL water was added. The mixture was stirred at room temperature for 1 hour, added to a 750 mL volume of crushed ice, and the pH of the solution was brought to pH 6.0 with 6M HCl. After repeated ultrafiltration against a 3 kDa MWCO ultrafiltration membrane, the product was lyophilized. The yield was 126.21 g of recovered solid carboxymethyl reduced dextran T10 (sodium salt), having a carboxyl content of approximately 130 micromoles carboxyl per gram product as determined by titration (Table 7).

Example 21

Carboxymethyl Reduced Dextran CMRD T10 Using the Low Dextran High Base Method

Reduced dextran T10 (150 g) was dissolved in 720 mL water, and 720 mL of 8M sodium hydroxide was added. The mixture was brought to 25° C., a solution of 26.6 g bromoacetic acid in 140 mL water was added, and the mixture was stirred at room temperature for 1 hour and added to a 750 mL volume of crushed ice. The pH of the solution was brought to pH 6.0 with 6M HCl. After repeated ultrafiltration against a 3 kDa MWCO ultrafiltration membrane, the product was lyophilized. The yield was not determined. The recovered solid, carboxymethyl reduced dextran T10 (sodium salt), showed a carboxyl content of approximately 280 micromoles carboxyl per gram product as determined by titration (Table 7).

Example 22

Carboxymethyl Reduced Dextran CMRD T10 Using the Low Dextran High Base Method Reduced dextran T10 (15 g) was dissolved in 72 mL of water, and 72 mL of 8M sodium hydroxide was added. The mixture was brought to 25° C., and a solution of 3.45 g of bromoacetic acid in 8 mL water was added. The mixture was stirred at room temperature for 1 hour, and then added to a 75 mL volume of crushed ice. The pH of the solution was brought to pH 6.0 with 6M HCl. After repeated ultrafiltrations against 3 kDa MWCO ultrafiltration membranes, the product was lyophilized. The yield was 9.4 g of recovered solid carboxymethyl reduced dextran T10 (sodium salt), having a carboxyl content of approximately 450 micromoles carboxyl per gram product as determined by titration (Table 7).

Example 23

Carboxymethyl Reduced Dextran CMRD T10 Using the Low Dextran High Base Method Reduced dextran T10 (150 g) was dissolved in 720 mL of water, and 720 mL of 8M sodium hydroxide was added. The mixture was brought to 25° C., and a solution of 58.8 g of bromoacetic acid in 140 mL water was added. The mixture was stirred at room temperature for 1 hour, and was then added to a 750 mL volume of crushed ice. The pH of the solution was brought to pH 6.0 using 6M HCl. After repeated ultrafiltrations against a 3 kDa MWCO ultrafiltration membrane, the product was lyophilized. The yield was 127.88 g of the recovered solid carboxymethyl reduced dextran T10 (sodium salt), having a carboxyl content of approximately 580 micromoles carboxyl per gram product as determined by titration (Table 7).

Table 7 shows that the extent of carboxymethyl substitution observed was a function of the amount of bromoacetic acid used in the reaction. The data show that generally increasing the amount of bromoacetic acid in the reaction resulted in increasing levels of COOH in the product. The yield of carboxymethyl incorporation was also affected by conditions such as scale of the reaction, for example, as in Examples 22 and 23.

TABLE 7

Preparation of CMRDs with varying extents of carboxymethylation.

| Example | dextran mg/g | NaOH mg/g | bromoacetic acid mg/g | micromoles COOH/g product |
|---------|--------------|-----------|----------------------|---------------------------|
| 19 | 75 | 115.7 | 5.77 | 110 |
| 20 | 75 | 115.7 | 5.77 | 130 |
| 21 | 73 | 111.6 | 16.7 | 280 |

TABLE 7-continued

Preparation of CMRDs with varying extents of carboxymethylation.

| Example | dextran mg/g | NaOH mg/g | bromoacetic acid mg/g | micromoles COOH/g product |
|---------|--------------|-----------|----------------------|---------------------------|
| 22 | 70 | 107.2 | 27.3 | 450 |
| 23 | 70 | 107.2 | 27.3 | 580 |

Example 24

Carboxymethyl Reduced Dextran T10 from a Commercial Source

Carboxymethyl reduced dextran was purchased from Amersham-Pharmacia. The solid showed a carboxyl content of approximately 1887 micromoles carboxyl per gram product as determined by titration.

Examples 25-27 describe synthesis of carboxymethyl dextran from native, non-reduced dextran T-10, T-40, and T-70, respectively.

Example 25

Carboxymethyl Dextran T10

The following solutions were prepared and cooled to 5° C.: Solution A: 105.2 g sodium hydroxide in 250 mL water; Solution B: 58.0 g bromoacetic acid in 142.5 mL water; and Solution C, 75.7 g dextran T10 in 187.5 mL water.

To Solution C and Solution A were added sodium hydroxide (14.4 g) dissolved in 187.5 mL water while maintaining the temperature of the solution below 25° C. Solution B was added, keeping the temperature below 25° C., and the resulting solution was stirred for 2 hours at room temperature, then was neutralized to pH 7.5 with 6M HCl (cooled to 5° C.) while maintaining the solution temperature below 35° C. The mixture was passed through a 0.2 µm pore size filter, and diluted to 2 liters. The product was purified by repeated ultrafiltration against a 3 kDa MWCO ultrafiltration membrane, 0.2 µm filtered again, and lyophilized. The yield was 53.17 g, and the recovered solid carboxymethyl dextran T10 (sodium salt) showed a carboxyl content of approximately 1220 micromoles carboxyl per gram product as determined by titration.

Example 26

Carboxymethyl Dextran T40

The following solutions were prepared and cooled to 5° C.: Solution A: 154 g sodium hydroxide in 480 mL water; Solution B: 77 g bromoacetic acid in 260 mL water; and Solution C: 100 g dextran T40 in 400 mL water.

Solution A was added to Solution C all at once. After 5 min, Solution B was added and the combined solution was stirred for 120 min while the temperature was maintained between 20° C. and 25° C. The mixture was neutralized with 6 M HCl, was 0.2 µm filtered, and diluted to 2 liters. The product was purified by repeated ultrafiltration against 3 kDa MWCO ultrafiltration membranes, was 0.2 µm filtered and was lyophilized. The yield was 105.1 g of recovered solid carboxymethyl dextran T40 (sodium salt), which showed a carboxyl content of about 1390 micromoles carboxyl per gram product as determined by titration.

Example 27

Carboxymethyl Dextran T70

The following solutions were prepared and cooled to 5° C.: Solution A: 154 g sodium hydroxide in 480 mL water; Solution B: 77 g bromoacetic acid 260 mL water; and Solution C: 100 g dextran T70 in 400 mL water.

Solution A was added to Solution C all at once. After 5 min, Solution B was added, and the combined solution was stirred, maintaining the temperature between 20° C. and 25° C. using an ice bath. After 120 min, the solution was neutralized with 6 M HCl. The solution was 0.2 μm filtered, and diluted to 2 liters. The product was purified by repeated ultrafiltration against 3 kDa MWCO ultrafiltration membranes, was 0.2 μm filtered again and was lyophilized. The yield was 106.9 g of recovered solid carboxymethyl dextran T70 (sodium salt), having a carboxyl content of about 1380 micromoles carboxyl per gram product as determined by titration.

General procedure for the preparation of superparamagnetic colloids for comparison of the properties of USPIO preparations coated with either of reduced or non-reduced polysaccharides.

Examples 28-35 were conducted to compare polysaccharide coated iron oxide products obtained from pairs of native and reduced polysaccharides of identical molecular weights. Identical procedures were utilized for the preparation of USPIO colloids for each pair of native and reduced polysaccharide of identical molecular weight. In particular, the same polysaccharide to iron ratio and iron concentration was used for each molecular weight pair. The polysaccharide to iron ratio and iron concentration utilized for each native and reduced polysaccharide pair were chosen to yield a 0.2 μm filterable USPIO with a diameter of less than 30 nm and a magnetic susceptibility of greater than $20,000 \times 10^{-6}$ cgs with the reduced polysaccharide.

The general procedure involved addition of excess ammonium hydroxide to a solution of iron salts ($Fe^{+3}/Fe^{+2}$) and polysaccharide, followed by heating, and performing six cycles of ultrafiltration against water using a 100 kDa MWCO membrane filter. After ultrafiltration, the USPIO preparations formed with reduced polysaccharide were filtered through a 0.2 μm filter and stored at 4° C.

It was observed that for iron oxides prepared with a native polysaccharide, only the native dextran T10 coated iron oxide was filterable through a 0.2 μm filter. The size and magnetic susceptibility, except for those samples containing particulate materials, were then measured. Particle sizes were determined by measurement of dynamic light scattering in a Microtrac® UPA instrument (Honeywell IAC Microtrac, Fort Washington, Pa.) and are reported as the mean volume diameter (MVD). Magnetic susceptibility was determined with a Mathey Johnson magnetic susceptibility balance. Iron concentrations were determined with a bipyridyl assay (Kumar K., *J. Liq. Chromatogr. Relat. Technol.*, 1997, 20, 3351-3364).

Example 28

Preparation of Reduced Dextran T1 Coated USPIO

Reduced dextran T1 (1.7 g) was dissolved in 20 mL water, and a solution of 3 g of ferric chloride hexahydrate and 1.5 g of ferrous chloride tetrahydrate in 32 g water was added. The mixture was purged with nitrogen for 30 min, cooled to 5° C., and 12.7 g of 28% ammonium hydroxide was added with stirring during a 2 min period. The mixture was heated to 60° C., maintained at this temperature for 40 min, then incubated at 80° C. for 2 h. The product was subjected to six cycles of ultrafiltration against water using a 100 kDa MWCO membrane filter. After ultrafiltration, the product was filtered through a 0.2 μm filter and stored at 4° C. The product was observed to have the following properties: the mean volume diameter (determined by use of a Microtrac Particle Size Analyzer) was 18 nm; the magnetic susceptibility was $13,323 \times 10^{-6}$ cgs/g Fe.

Example 29

Preparation of Native Dextran T1 Coated Iron Oxide

Native dextran T1 iron oxide was prepared by the method described above for the reduced dextran in Example 28 except that native dextran T1 was used instead of reduced dextran T1. The product was observed to have the following properties: the mean volume diameter (determined by use of a Microtrac Particle Size Analyzer) was 2764 nm; the magnetic susceptibility was $1,953 \times 10^{-6}$ cgs/g Fe.

Example 30

Preparation of Reduced Dextran T5 Coated USPIO

Reduced dextran T5 (0.45 g) was dissolved in 13 mL water, and a solution of 0.5 g of ferric chloride hexahydrate and 0.25 g of ferrous chloride tetrahydrate in 4.5 g water was added. The mixture was purged with nitrogen for 30 min, cooled to 5° C., and 1.42 g of 28% ammonium hydroxide was added with stirring during a 2 min period. The mixture was heated at 80° C. for 2 h, and was purified as described in Example 28. The product was observed to have the following properties: the mean volume diameter (determined by use of a Microtrac Particle Size Analyzer) was 16 nm; the magnetic susceptibility was $33,943 \times 10^{-6}$ cgs/g Fe.

Example 31

Preparation of Native Dextran T5 Coated Iron Oxide

Native dextran T5 iron oxide was prepared by the method described above for the reduced dextran in Example 30 except that native dextran T5 was used instead of reduced dextran T5. The product was observed to have the following properties: the mean volume diameter (determined by use of a Microtrac Particle Size Analyzer) was 1,916 nm.

Example 32

Preparation of Reduced Dextran T10 Coated USPIO

Reduced dextran T10 (2.7 g) was dissolved in 70 mL water, and a solution of 2.0 g ferric chloride hexahydrate and 1.0 g ferrous chloride tetrahydrate in 27 g water was added. The mixture was purged with nitrogen for 30 min, cooled to 5° C., and 8.5 g of 28% ammonium hydroxide was added with stirring during a 2 min period. The mixture was heated at 80° C. for 2 h and purified as described in Example 28. The product was observed to have the following properties: the mean volume diameter (determined by use of a Microtrac Particle Size Analyzer) was 12 nm; the magnetic susceptibility was $31,743 \times 10^{-6}$ cgs/g Fe.

Example 33

Preparation of Native Dextran T10 Coated Iron Oxide

Native dextran T10 iron oxide was prepared by the method described above for the reduced dextran in Example 32 except that native dextran T10 was used instead of reduced dextran T10. The product was observed to have the following properties: the mean volume diameter (determined by use of a Microtrac Particle Size Analyzer) was 757 ηm; the magnetic susceptibility was $31,252 \times 10^{-6}$ cgs/g Fe.

Example 34

Preparation of Reduced Pullulan Coated USPIO

Reduced pullulan (0.045 g) was dissolved in 0.4 mL water, and a solution of 0.106 g ferric chloride hexahydrate and 0.05 g ferrous chloride tetrahydrate in 1.3 g water was added. The mixture was purged with nitrogen for 30 min, cooled to 5° C., and 0.044 g of 28% ammonium hydroxide was added with stirring during a 2 min period. The mixture was heated at 80° C. for 0.67 h and purified as described in Example 28. The product was observed to have the following properties: the mean volume diameter (determined by use of a Microtrac Particle Size Analyzer) was 20 nm; the magnetic susceptibility was $27,066 \times 10^{-6}$ cgs/g Fe.

Example 35

Preparation of Native Pullulan Coated Iron Oxide

Native pullulan iron oxide was prepared by the method described above for the reduced pullulan in Example 34 except that native pullulan was used instead of reduced pullulan. The product was observed to have the following properties: the mean volume diameter (determined by use of a Microtrac Particle Size Analyzer) was 1,184 nm.

Properties of Iron Oxide Preparations Obtained Using Reduced in Comparison to Native Polysaccharides (Comparison of Data Obtained from Examples 28-35).

In general for MRI contrast agents, an iron oxide contrast agent particle of small size is preferred, for example, a particle having a diameter in the range of 10 to 50 nm. Further, an iron oxide of greater magnetic susceptibility, and of greater homogeneity is preferred.

It is observed from the data of Examples 28-35 that the presence of a reduced terminal sugar of a polysaccharide (reduced polysaccharide) used to coat an iron oxide had an unexpected and substantial effect on the diameter of particles of each of the resulting colloids, compared to similarly produced iron oxides made using native non-reduced polysaccharide. Table 8 shows the size of particles formed for each pair of native and reduced polysaccharides, as indicated by the mean volume diameters (MVD). The concentrations of reduced and native polysaccharides were kept constant within each molecular weight group. Concentrations were selected to optimize the synthesis of USPIO with reduced polysaccharide. For all polysaccharides, use of the native non-reduced polysaccharide consistently produced a larger particle than did use of the reduced dextran, so that the reduced polysaccharide consistently gave the preferred smaller particle.

Further, for each pair of polysaccharides of a given molecular weight that was synthesized and tested, the USPIO preparation coated with reduced polysaccharides demonstrated a higher magnetic susceptibility value than the corresponding iron oxide preparation synthesized with native polysaccharide, except for colloids obtained with dextran T10 for which magnetic susceptibilities of reduced and native coatings were equivalent.

These data indicate that use of a reduced polysaccharide in preparation of coated USPIO colloids yields preferred particles of small size, without loss of magnetic susceptibility. The data demonstrate the surprising effect that reduction of the aldehyde of a polysaccharide has upon the synthesis of a polysaccharide-coated USPIO.

TABLE 8

Comparison of properties of iron oxides made with native or reduced polysaccharides under conditions that form a USPIO with reduced polysaccharides.

| Example | poly-saccharide | ratio of poly-saccharide per Fe, g/g | MVD nm reduced | MVD nm native | MS[a] reduced | MS[a] native |
|---|---|---|---|---|---|---|
| 28, 29 | dextran T1 | 1.6 | 18 | 2,764 | 13,323 | 1,953 |
| 30, 31 | dextran T5 | 2.9 | 16 | 1,916 | 33,943 | b |
| 32, 33 | dextran T10 | 4.6 | 21 | 757 | 31,743 | 31,252 |
| 34, 35 | pullulan | 3.9 | 20 | 1,184 | 27,066 | b |

Magnetic susceptibility ($\times 10^{-6}$ cgs/g Fe)
[b]The sample was particulate, could not be filtered through a 0.2 μm filter, and magnetic susceptibility was not determined.

Properties of Iron Oxides Prepared with Native Non-Reduced T1, T5 and T10 Dextrans Of Mean Volume Diameter Less than 30 nm.

Examples 36, 38 and 40 and 37, 39 and 41 show the preparation of iron oxides obtained from native dextran T1, T5, and T10 and from PEG4000, PEG60000, and PEG10000, respectively. Colloids were prepared using non-reduced (native) dextrans as described for reduced dextrans (Examples 28, 30, and 32), except that the preparation of these native non-reduced dextran particles required about 10- to 34-fold more dextran than their corresponding reduced dextran counterpart to produce iron oxides of corresponding size. The requirement for increased dextran usage is shown by comparing the dextran to iron ratio of the products for corresponding molecular weight pairs of iron oxides shown (Table 9).

The data show that the magnetic properties, and the efficiency of dextran use during synthesis, of iron oxide particles prepared with each of native dextrans T1, T5, and T10 were inferior compared with corresponding properties of particles prepared with each counterpart reduced dextran.

Examples 36

Preparation of Iron Oxide Coated with Native T1 Dextran

A mixture of 0.42 g ferric chloride hexahydrate, 0.21 g ferrous chloride tetrahydrate, and 7.27 g water was filtered through a 0.2 μm filter. A 1.0 g portion of this mixture was added to 10 mL of an aqueous solution of 0.1 g dextran T1/g water. The mixture was purged with nitrogen before adding 0.22 mL of 28% ammonium hydroxide solution. The mixture was heated at 80° C. for 1 hour, cooled to room temperature and filtered through a 0.2 μm filter. The product was observed

Example 37

Preparation of Iron Oxide Coated with the Polyetherl Polyethylene Glycol 4000 (PEG4000)

A mixture of 0.42 g ferric chloride hexahydrate, 0.21 g ferrous chloride tetrahydrate, and 7.27 g water is filtered through a 0.2 μm filter. A 1.0 g portion of this mixture is added to 10 mL of an aqueous solution of 0.1 g polyethylene glyco 11000/g water (PEG100/g water). The mixture is purged with nitrogen before adding 0.22 mL of 28% ammonium hydroxide solution. The mixture is heated at 80° C. for about 1 hour, cooled to room temperature and filtered through a 0.2 μm filter. The mean volume diameter (determined by use of a Microtrac Particle Size Analyzer) and the magnetic susceptibility in cgs/g Fe are then determined.

Examples 38

Preparation of Iron Oxide Coated with Native T5 Dextran

Dextran T5 (0.8 g) was dissolved in 9 mL water, and added to 0.63 mL of a 0.2 μm filtered solution of 51.8 mg ferric chloride hexahydrate and 25.9 mg ferrous chloride tetrahydrate in 9.2 mL water. The mixture was purged with nitrogen before adding 1.4 mL 28% ammonium hydroxide solution. The mixture was heated at 80° C. for 1 hour, cooled to room temperature, and filtered through a 0.2 μm filter. The product was observed to have the following properties: the mean volume diameter (determined by use of a Microtrac Particle Size Analyzer) was 20 μm; the magnetic susceptibility was $1285 \times 10^{-6}$ cgs/g Fe.

Examples 39

Preparation of Iron Oxide Coated with PEG6000

PEG6000 (0.8 g) is dissolved in 9 mL water, and added to 0.63 mL of a 0.2 μm filtered solution of 51.8 mg ferric chloride hexahydrate and 25.9 mg ferrous chloride tetrahydrate in 9.2 mL water. The mixture is purged with nitrogen before adding 1.4 mL 28% ammonium hydroxide solution. The mixture is heated at 80° C. for about 1 hour, cooled to room temperature, and filtered through a 0.2 μm filter. The mean volume diameter (determined by use of a Microtrac Particle Size Analyzer) and the magnetic susceptibility in cgs/g Fe are then determined.

Example 40

Preparation of Iron Oxide Coated with Native T10 Dextran

Dextran T10 (9420 g) was dissolved in 14915 g water. A 14915 g portion of this mixture was filtered through a 0.2 μm filter, and added to the reaction vessel. Ferric chloride hexahydrate (891 g) was dissolved in 713 water. A 1129 g portion was 0.2 μm filtered and added to the reaction vessel containing the dextran. The mixture was cooled to 5° C. with stirring overnight while bubbling nitrogen through the mixture. Before the last 30 min. of the nitrogen purge, a 580 g portion of a 0.2 μm filtered solution of 359 g ferrous chloride tetrahydrate in 477 g water was added. To this mixture was added 786 g of 28% ammonium hydroxide solution, cooled to 5° C. The mixture was heated to 80° C., incubated at 80° C. for 2 hours, and then poured into 80 liters of water heated to 80° C. The mixture was allowed to cool overnight, 0.2 μm filtered, and purified by ultrafiltration using a 100 kDa ultrafiltration membrane. The product was 0.2 μm filtered. The product was observed to have the following properties: the mean volume diameter (determined by use of a Microtrac Particle Size Analyzer) was 21 nm; the magnetic susceptibility was $32,712 \times 10^{-6}$ cgs/g Fe.

TABLE 9

Magnetic susceptibility and particle size properties of polysaccharide coated iron oxides: a comparison of native dextrans (Examples 36-40) with respective reduced dextrans (Examples 28, 30, and 32) under conditions to give particles of less than 30 nm MVD with maximum magnetic susceptibility

| Example | dextran type | dextran/Fe (g/g)[b] | MVD (nm) | MS[a] |
|---|---|---|---|---|
| iron oxides prepared with native dextran ||||||
| 36 | dextran T1 | 55 | 27 | 2,325 |
| 38 | dextran T5 | 44 | 20 | 1,285 |
| 40 | dextran T10 | 44 | 21 | 32,712 |
| iron oxides prepared with reduced dextran ||||||
| 28 | dextran T1 | 1.6 | 18 | 13,323 |
| 30 | dextran T5 | 2.9 | 16 | 33,943 |
| 32 | dextran T10 | 4.6 | 12 | 31,743 |

[a]Magnetic susceptibility ($\times 10^{-6}$ cgs/g Fe)
[b]The polysaccharide/Fe ratio was varied for each dextran in order to obtain a USPIO with a MVD of less than or equal to 30 nm.

Example 41

Preparation of Iron Oxide Coated with PEG10000

PEG10000 (9000 g) is dissolved in 14000 g water. A 14000-g portion of this mixture is filtered through a 0.2 μm filter, and added to the reaction vessel. Ferric chloride hexahydrate (890 g) is dissolved in 710 g water. A 1130-g portion is 0.2 μm filtered and added to the reaction vessel containing the PEG10000. The mixture is cooled to 5° C. with stirring overnight while bubbling nitrogen through the mixture. Before the last 30 min. of the nitrogen purge, a 580 g portion of a 0.2 μm-filtered solution of 360 g ferrous chloride tetrahydrate in 480 g water is added. To this mixture is added 790 g of a 28% ammonium hydroxide solution, and the mixture is then cooled to 5° C. The mixture is heated to 80° C., incubated at 80° C. for 2 hours, and then poured into 80 liters of water heated to 80° C. The mixture is allowed to cool overnight, 0.2 μm filtered, and purified by ultrafiltration using a 100-kDa ultrafiltration membrane. The product is then 0.2 μm filtered. The mean volume diameter (determined by use of a Microtrac Particle Size Analyzer) and the magnetic susceptibility in cgs/g Fe are then determined.

Preparation USPIOs Coated with Carboxymethyl Native Dextran T10 and Carboxymethyl Reduced Dextran T10 Containing Varying Degrees of Carboxymethylation.

Examples 42 and 43 describe preparation of USPIO coated with carboxymethyl native and reduced dextran T10, respectively. Examples 44-48 describe the synthesis of USPIO compositions coated with carboxymethyl reduced dextran T10 preparations, containing varying degrees of carboxymethylation. Examples 49-53 describe the solubility of preparations containing ferric chloride and carboxymethyl reduced dextran T10 containing varying degrees of carboxymethylation.

Example 42

Preparation of USPIO Coated with Carboxymethyl Dextran T10

Carboxymethyl dextran T10 (60 g, prepared by the method Example 25) was dissolved in 532 g water. A solution of 14.7 g ferric chloride hexahydrate, 7.2 g ferrous chloride tetrahydrate, and 100 mL water, was filtered through a 0.2 μm, and added. The mixture was cooled to 10° C., purged with nitrogen, and 52.2 mL of 28% ammonium hydroxide solution was added with stirring. The mixture was heated to 75° C., maintained at 75° C. for 30 min, diluted with 2.5 liter water, and filtered through a 0.2 μm filter. The product was purified by repeated ultrafiltration against a 100 kDa MWCO membrane, concentrated to 20 mg Fe/mL, and again filtered through a 0.2 μm filter. The product was observed to have the following properties: MVD (determined by use of a Microtrac Particle Size Analyzer) was 19 nm; the magnetic susceptibility was $27,835 \times 10^{-6}$ cgs/g Fe; and the carboxyl content was 1,220 micromoles per gram of the CMRD. To determine stability in response to autoclaving, a sample of the product was placed in a sealed 5 mL glass vial, and heated to 121° C. for 30 min (see Table 13).

Example 43

Preparation of USPIO Coated with Carboxymethyl Reduced Dextran T10

Reduced carboxymethyl dextran T10 (40 g prepared in Example 14) was dissolved in 1,038 mL water and was filtered through a 0.2 μm pore size filter. A 0.2 μm filtered solution of 30 g ferric chloride hexahydrate and 15 g of ferrous chloride tetrahydrate in 374 mL of water was added to the dextran, with a 31 mL water wash. The solution was cooled to 10° C., and 114 g of 28% ammonium hydroxide was added. The colloidal mixture was heated to 78° C. and maintained at that temperature for one hour. The solution was then diluted to 3 liter with water, cooled to 10° C., and ultrafiltered 6 times with a YM-100 filter membrane (100 kDa MWCO). A final concentration of 21.1 mg Fe/g was obtained. The product was observed to have the following properties: the mean volume diameter (Microtrac Particle Size Analyzer) was 21 nm; the magnetic susceptibility was $32,732 \times 10^{-6}$ cgs/g Fe; and the carboxyl content was 1,265 micromoles per gram of the CMRD. The content of the particle was determined to be about 50% Fe and 50% dextran. To determine stability in response to autoclaving, a sample of the product was placed in a sealed 5 mL glass vial, and heated to 121° C. for 30 min (see Table 13).

Example 44

Preparation of USPIO Coated with Carboxymethyl Reduced Dextran T10 Having 110 Micromoles Carboxyl Per Gram Carboxymethyl reduced dextran T10 (4 g, prepared in Example 19) was dissolved in 85 mL water. To this was added a 0.2 μm filtered mixture of 2.99 g ferric chloride hexahydrate, 1.49 g ferrous chloride tetrahydrate, and 37.3 mL water. The mixture was cooled to 10° C., purged with nitrogen, 11.4 g of 28% ammonium hydroxide solution was added with stirring the mixture was heated to 90° C., maintained at 78° C. for 60 minutes, and then maintained at 78° C. while bubbling air through the mixture. The mixture was diluted with 1.5 liters of water, and was filtered through a 0.2 μm filter. The product was purified by repeated ultrafiltration against a 100 kDa MWCO membrane and again filtered through a 0.2 μm filter.

Example 45

Preparation of USPIO Coated with Carboxymethyl Reduced Dextran T10 Having 130 Micromoles Carboxyl Per Gram Carboxymethyl reduced dextran T10 (40 g, prepared in Example 20) was dissolved in 850 mL water. To this was added a 0.2 μm filtered mixture of 29.9 g ferric chloride hexahydrate, 14.9 g ferrous chloride tetrahydrate, and 373 mL water. The mixture was cooled to 10° C., purged with nitrogen, 114 mL of 28% ammonium hydroxide solution was added with stirring, the mixture was heated to 90° C., maintained at 78° C. for 60 min, and then maintained at 78° C. while bubbling air through the mixture. The mixture was diluted with 1.5 liters of water, and filtered through a 0.2 μm filter. The product was purified by repeated ultrafiltration against a 100 kDa MWCO membrane, concentrated to 20 mg Fe/mL, and again filtered through a 0.2 μm filter.

Example 46

Preparation of USPIO Coated with Carboxymethyl Reduced Dextran T10 Having 280 Micromoles Carboxyl Per Gram Carboxymethyl reduced dextran T10 (4 g, prepared in Example 21) was dissolved in 85 mL water. To this was added a 0.2 μm filtered mixture of 2.99 g ferric chloride hexahydrate, 1.49 g ferrous chloride tetrahydrate, and 37.3 mL water. The mixture was cooled to 10° C., and purged with nitrogen. To the mixture was added with stirring 11.4 g of 28% ammonium hydroxide solution, the mixture was heated to 90° C., maintained at 78° C. for 60 min, and then maintained at 78° C. while air was bubbled through the mixture. The mixture was diluted with 1.5 liters of water, and filtered through a 0.2 μm filter. The product was purified by repeated ultrafiltration against a 100 kDa MWCO membrane, followed by filtration through a 0.2 μm filter.

Example 47

Preparation of USPIO Coated with Carboxymethyl Reduced Dextran T10 Having 450 Micromoles Carboxyl Per Gram Carboxymethyl reduced dextran T10 (4 g, prepared in Example 22) was dissolved in 85 mL water. To this was added a 0.2 μm filtered solution of 2.99 g ferric chloride hexahydrate, 1.49 g ferrous chloride tetrahydrate, and 37.3 mL water. The mixture was cooled to 10° C., and purged with nitrogen before adding 11.4 g of 28% ammonium hydroxide solution with stirring. The mixture was heated to 90° C., maintained at 78° C. for 60 min, and then maintained at 78° C. while air was bubbled through the mixture. The mixture was diluted with 1.5 liters of water, filtered through a 0.2 μm filter, and was purified by repeated ultrafiltration against a 100 kDa MWCO membrane followed by filtration through a 0.2 μm filter.

Example 48

Preparation of USPIO Coated with Carboxymethyl Reduced Dextran T10 Having 580 Micromoles Carboxyl Per Gram Carboxymethyl reduced dextran T10 (40 g, prepared in Example 23) was dissolved in 85 mL water. To this was added a 0.2 μm filtered solution of 29.9 g ferric chloride hexahydrate, 14.9 g ferrous chloride tetrahydrate, and 373 mL water. The mixture was cooled to 10° C., purged with nitrogen, 11.4 g of 28% ammonium hydroxide solution with stirring. The mixture was heated to 90° C., maintained at 78° C. for 60 min, then maintained at 78° C. while bubbling air through the mixture. The mixture was diluted with 1.5 liters of water and filtered through a 0.2 μm filter, and was purified by repeated ultra-filtration against a 100 kDa MWCO membrane followed by filtration through a 0.2-μm filter.

The effect of degree of carboxymethylation of the CMRD coated USPIOs on colloid size was compared. Examples 43-48, Table 10. The MVD values of the resulting colloids were reasonably uniform between CMRD preparations containing 110 to 1265 micromoles of carboxyl per gram of product.

TABLE 10

Particle sizes of USPIO colloids prepared with dextran T10 CMRDs having varying degrees of carboxymethylation.

| Example # | micromoles COOH/g dextran | mean volume diameter, nm |
|---|---|---|
| 44 | 110 | 12 |
| 45 | 130 | 15 |
| 46 | 280 | 18 |
| 47 | 450 | 16 |
| 48 | 580 | 20 |
| 49 | 1265 | 21 |

Example 49

Mixing of Carboxymethyl Reduced Dextran T10 Having 1,108 Micromoles Carboxyl Per Gram with Ferric Chloride Solution As a step in particle synthesis, ferric chloride (0.3 g) was dissolved in 15 mL water and was filtered through a 0.2 μm pore size filter. Carboxymethyl reduced dextran (prepared in Example 15) was added, the mixture was shaken, and was cooled to 10° C. No precipitate was observed.

Example 50

Mixing of Carboxymethyl Reduced Dextran T10 Having 1,262 Micromoles Carboxyl Per Gram with Ferric Chloride Solution Ferric chloride (0.3 g) was dissolved in 15 mL water and was filtered through a 0.2 μm pore size filter. Carboxymethyl reduced dextran (prepared in Example 16) was added, the mixture was shaken, and was cooled to 10° C. No precipitate was observed.

Example 51

Mixing of Carboxymethyl Reduced Dextran T10 Having 1,404 Micromoles Carboxyl Per Gram with Ferric Chloride Solution Ferric chloride (0.3 g) was dissolved in 15 mL water and was filtered through a 0.2 μm pore size filter. Carboxymethyl reduced dextran (prepared in Example 17) was added, the mixture was shaken, and was cooled to 10° C. No precipitate was observed.

Example 52

Mixing of Carboxymethyl Reduced Dextran T10 Having 1,528 Micromoles Carboxyl Per Gram with Ferric Chloride Solution Ferric chloride (0.3 g) was dissolved in 15 mL water and was filtered through a 0.2 μm pore size filter. Carboxymethyl reduced dextran (prepared in Example 18) was added, the mixture was shaken, and was cooled to 5° C. An orange white precipitate was observed.

Example 53

Mixing of Carboxymethyl Reduced Dextran T10 Having 1,887 Micromoles Carboxyl Per Gram with Ferric Chloride Ferric chloride hexahydrate (30.3 g) and ferrous chloride (14.8 g) were dissolved in 402.9 mL water and filtered through a 0.2 μm pore size filter. Carboxymethyl reduced dextran T10 (40.3 g in 1,033 ml, prepared in Example 24) was added, the mixture was shaken, and was cooled to 5° C. An orange white precipitate was observed.

The effect of varying the degree of carboxymethylation of CMRDs on the first step of the CMRD-USPIO synthesis, i.e., combining the aqueous mixtures of CMRD with the iron chloride solutions, was analyzed. The various CMRD preparations were mixed with iron salts at a fixed iron concentration, the CMRD preparations differing only in degree of carboxymethylation as described in Examples 49-53. From 1,108 to 1,404 micromoles carboxyl per gram dextran, the CMRD formed a homogeneous mixture in the presence of ferric chloride (Table 11).

TABLE 7

Precipitation of CMRDs having varying levels of carboxyl groups after addition of iron salts from mixtures of CMRD (25 mg/g solution) and ferric chloride (19 mg/g solution).

| Example # | micromoles COOH/g dextran | precipitate |
|---|---|---|
| 49 | 1,108 | no |
| 50 | 1,262 | no |
| 43 | 1,265 | no |
| 51 | 1,404 | no |
| 52 | 1,528 | yes, at 5° C. |
| 53 | 1,887 | yes, at 25° C. |

At greater than 1,404 micromoles carboxyl per gram dextran, addition of ferric chloride under the conditions and concentrations of the USPIO synthesis to the CMRD solution produced an orange white precipitate. Even at higher temperatures, where many compounds can be soluble, the precipitates persisted. The data in Table 11 shows that there is an upper level in modification of CMRD that can be used in the preferred method of CMRD-USPIO synthesis.

Example 54

Synthesis of Iron Oxide Sols and their Stabilization with Native and Reduced Dextrans and CMRD: Preparation of a Magnetic Sol To prepare a magnetic sol, 60 g of 28% of ammonium hydroxide at 25° C. was added to a solution having 30.0 g ferric chloride hexahydrate and 15.1 g ferrous chloride tetrahydrate in 321 g of water. After 5 minutes of mixing, sufficient concentrated HCl was added to obtain a pH of 1.6. The sol was ultrafiltered with a 100 kDa MWCO membrane filter to achieve a pH of 3.25, using water as diluent. The magnetic sol was passed through a filter of pore size 0.2 μm, then concentrated to 50 mg Fe/g, and stored at 5° C. The yield of iron was 55%, and the product was observed to have an MVD of 16 nm.

Example 55

Synthesis of Iron Oxide Sols and their Stabilization with Native and Reduced Dextrans and CMRD: Preparation of a Non-Magnetic Sol To a solution of 2.9 g of ferric chloride hexahydrate in 30 mL of water was added 10 mL of 10 M NaOH. The mixture was stirred for 5 min, diluted to 200 mL with water, and the product was collected by filtration. The residue was again mixed with water and filtered. The residue was added to 40 mL water and the pH was adjusted to 2.0. The product was observed to have an MVD of 10 nm.

Example 56

Synthesis of Iron Oxide Sols and their Stabilization with Native and Reduced Dextrans and CMRD: Coating of a Magnetic Sol with Reduced Dextran T10

Reduced dextran T10 (60 mg; Example 12) was dissolved in 1.74 mL water and combined with 0.24 mL of magnetic sol (13 mg Fe) prepared according to Example 54. The mixture was incubated for 15 min, and the pH was adjusted to 7.4 with sodium hydroxide. The particle size (MVD) was determined to be 85 nm.

Example 57

Synthesis of Iron Oxide Sols and their Stabilization with Native and Reduced Dextrans and CMRD: Coating of a Magnetic Sol with Native Dextran T10

Native dextran T10 (60.8 mg) was dissolved in 1.74 mL water, and combined with 0.24 mL of magnetic sol (13 mg Fe) prepared according to Example 54. The mixture was incubated for 15 min and the pH was adjusted to 7.4 with sodium hydroxide. The particle size (MVD) was determined to be 1,973 nm.

Example 58

Synthesis of Iron Oxide Sols and their Stabilization with Native and Reduced Dextrans and CMRD: Coating of a Magnetic Sol with CMRD T10

75 mg of CMRD T10 (Example 14) dissolved in 1.34 mL water was added to 0.66 mL of magnetic sol (33 mg Fe) prepared according to Example 54. The mixture was incubated for 15 min at 37° C., and the pH was adjusted to 7.95 (plus or minus 0.4) with sodium hydroxide. The mixture was concentrated using a 300 kDa ultrafiltration filter. The product was observed to have an MVD of 41 nm.

Example 59

Synthesis of Iron Oxide Sols and their Stabilization with Native and Reduced Dextrans and CMRD: Adjusting the pH of the Magnetic Sol to 7.4.

A magnetic sol as prepared in Example 54 was adjusted to a pH of 7.4. A precipitate was observed.

Example 60

Synthesis of Iron Oxide Sols and their Stabilization with Native and Reduced Dextrans and CMRD: Coating of a Non-Magnetic Sol with CMRD T10

A non-magnetic sol prepared according to Example 55 (35 ml) was added drop-wise to 35 mL of a 50 mg/g aqueous solution of CMRD T10 prepared according to Example 14. The pH was adjusted to 7.0 with 1 N NaOH, the solution was heated to boiling, cooled to room temperature, and was centrifuged at 6,000 rpm for 20 min. The supernatant was passed through a filter having a 0.2 μm pore size, and autoclaved at 121° C. for 30 min. The product was observed to have a MVD of 86 nm.

Examples 54-60 show that in the absence of a dextran, or in the presence of a native dextran, a gross iron precipitate forms. Only reduced dextran and CMRD yielded a magnetic sol as a stable colloid.

Example 61

Preparation of CMRD Coated Non-Magnetic Iron Oxide Colloid Using Base Co-Precipitation of Ferric Chloride and CMRD Carboxymethyl reduced dextran T10 (19.2 g) (Example 14) was dissolved in 300 g water, was filtered through a 0.2 μm filter, and an additional 160.8 g of water was added. This solution was added to 120 mL of 0.2 μm filtered aqueous 0.3 M ferric chloridehexahydrate. To this mixture was added 32 mL of aqueous 6N sodium hydroxide. The mixture was heated to 100° C. for 3 hours, cooled to room temperature, and ultrafiltered to a final volume of 50 mL. The product was observed to have an MVD of 30 nm. A portion of this material was placed in a bottle under nitrogen for 30 min at 121° C. The autoclaved product had an MVD of 69 nm.

Example 62

Effect of Autoclaving on Reduced and Native Dextran Colloids: Stability to Autoclaving of USPIOs Coated with Native Dextran and Reduced Dextran and CMRD Colloid preparations, each at a concentration of 20 mg Fe/g, were autoclaved for 30 min at 121° C. Following autoclaving, measurements were made of bound dextran that was calculated as the difference between total and free dextran, using a phenol/sulfuric acid assay. Free dextran was separated from the colloid by ultrafiltration. Table 12 shows that colloid preparations having USPIOs coated with a reduced dextran have greater stability than USPIOs coated with a native dextran. The reduced dextran coated USPIO maintained its small size following autoclaving, as the MVD of the post autoclaved material was increased only 1.3-fold compared to the MVD of the pre autoclaved material. In contrast, USPIO coated with native dextran increased in size 28-fold following autoclaving. The data show that following autoclaving, reduced dextran remains more tightly bound to the iron particle compared to native dextran.

A second type of increased stability achieved herein by use of reduced dextran to coat USPIO is the property of pH of the bulk solvent. The pH of USPIO coated with reduced dextran dropped 0.9 pH units following autoclaving, compared to a drop of 1.6 pH units for USPIO coated with native dextran.

Even greater stability to the autoclaving process was observed for particles coated with carboxymethyl reduced dextran compared to carboxymethyl native dextran. The data in Table 13 indicate that USPIO coated with carboxymethyl non-reduced native dextran showed a 10-50 fold increase in amount of particulate matter following autoclaving. In contrast, USPIO coated with carboxymethyl reduced dextran experienced no change in size or quantity of particulate matter upon autoclaving. Another indication of the stabilizing effect that the carboxymethyl reduced polysaccharide coatings confer on the colloid suspension and bulk solvent was the stability of the solvent pH. The data in both Tables 12 and 13 show that the particles coated with reduced dextran had significantly improved pH stability upon autoclaving, compared to those coated with native dextran.

TABLE 12

Effect of autoclaving on pH, size, and bound polysaccharide of colloids coated with native and reduced dextran.

| | | pre autoclaved | | | post autoclaved[a] | | |
|---|---|---|---|---|---|---|---|
| Example | dextran coating | H | bound dextran g/g | MVD nm | H | bound dextran g/g | MVD nm |
| 40 | native T10 | .0 | 0.79 | 21 | .5 | 0.56 | 587 |
| 32 | reduced T10 | .4 | 1.26 | 18 | .7 | 0.96 | 23 |

[a]Samples were prepared at a concentration of 20 mg iron per mL and autoclaved for 30 minutes at 121° C.

TABLE 13

Effect of autoclaving on pH, size, and particulates of colloids coated with carboxymethylated reduced and carboxymethylated native non-reduced dextran.

| | | | | particulates[a] | | | | |
|---|---|---|---|---|---|---|---|---|
| | | MVD | | pH | | >10 microns number/mL autoclaved | | >25 microns number/mL |
| Example | dextran coating | pre | pre | pre | pre | pre | pre | pre | post |
| 42 | CMD[b] | 9 | 8 | .5 | .8 | 5 | 33 | | 240 |
| 43 | CMRD[c] | 5 | 8 | .0 | .9 | | | | 5 |

[a]Particulates were determined by USP analysis.
[b]CMD, carboxymethyl dextran (native)
[c]CMRD, carboxymethyl reduced dextran
[d]Samples were prepared at a concentration of 20 mg iron per mL and autoclaved for 30 minutes at 121° C.

Example 63

Procedures for Determining Relaxation Properties of Various Contrast Agents

Nuclear magnetic (NM) measurements (0.47 T) were obtained in a Bruker Instruments pc120 table-top NM sample analyzer operating at 20 MHZ (Proton). Half a milliliter of each sample was placed in the 10 mm NM tubes for relaxivity measurements on the minispec. The placement of the sample in the sample chamber was optimized. The standards were run and their values recorded in the log.

Standard procedures were used for T1 and T2 determinations, and their values were recorded. T1 was measured using an inversion recovery technique. According to the IR technique, the sample is exposed to a 180° pulse and then a 90° pulse to put the magnetization in the plane of detection. After sampling, the time between the 180 and 90-degree pulses is changed, and sampled again. This is done for several durations. The resulting signals are governed by the equation $[M_\infty - M(t)]/M_\infty = (1 - \cos\theta)\exp(-t/T1)$. When a 3 parameter fit to data is performed, $M_\infty$, $\theta$, and T1 are calculated.

T2 was measured using the CPMG technique, where a linear train of 180° pulses of variable length is provided to the sample. The amplitude of every second echo is measured. A fit is performed on the accumulated data using a two parameter ($M_o$ and T2) fit. Where $M(t) = M_o \exp(-t/T2)$, a plot of $\ln(M(t))$ versus t is linear with a slope of $-1/T2$. The inverse of the T1 and T2 was graphed with respect to the iron concentration of the sample. From the slope of best fit line the relaxivity was determined.

TABLE 14

| | | Relaxivity | | | | |
|---|---|---|---|---|---|---|
| Material | Coating | Susceptibility | MW (kDa) | R1 | R2 | R2/R1 |
| Example 43 | reduced carboxymethyl dextran | 38,200 | 10 | 35.3 | 64.8 | 1.8 |
| Combidex ® | Dextran-T10 | 28,000 | 9.6 | 21.7 | 60.3 | 2.8 |
| Gd-DTPA | | 172 | | 4.5 | 5.7 | 1.3 |

Example 64

Toxicity of Reduced Dextran, Non-Reduced Dextran, and CMRD Coated Colloids in Rats An anaphylactic shock type of reaction to dextran can be exhibited by rats and by a small but significant fraction of the human population (Squire, J. R. et al., "Dextran, Its Properties and Use in Medicine," Charles C. Thomas, Springfield, Ill., 1955). The reaction resembles anaphylactic shock but does not require prior sensitization, and is characterized in rats by the rapid development of prostration, diffuse peripheral vasodilation, and edema of paws, snout and tongue (Voorhees, A. B. et al., *Proc. Soc. Exp. Biol. Med.* 1951, 76:254). When accompanied by barbiturate anesthesia, it produces marked hypotension and cyanosis (Hanna, C. H. et al., *Am. J. Physiol.* 1957, 191:615).

A procedure to measure the extent of rat paw edema response was employed to determine if the presence of reduced dextrans or their derivatives, rather than non-reduced native dextrans, in the coating of the iron oxide colloids could decrease or eliminate potential human adverse reactions upon intravenous injection. Rat paw edema was measured as the volume of the paw prior to and subsequent to injection of test material, using a plethysmometer, which is a differential volume measuring device. The dose of test material was injected, and a second reading was taken after a designated interval, and the percent change in paw volume was calculated. The dose administered in these studies was 100 mg Fe/kg body weight, a dose much greater than that used as an imaging agent in rats, pigs, and humans (see Examples 67-70).

The results observed following administration of iron oxides coated with each of reduced and non-reduced T10 dextrans are shown in Table 15. A marked decrease in the edematous anaphylactic response was observed in those rats which were administered a USPIO preparation having the reduced dextran or reduced dextran derivatives as a coating, compared to those rats administered a USPIO preparation having a native non-reduced dextran coating.

TABLE 15

Effect of native and reduced polysaccharide coated particles on rat edema.

| Example | coating and particle | % edema |
|---|---|---|
| 40 | native dextran coated USPIO | >50 |
| 32 | reduced dextran coated USPIO | 13 |
| 42 | carboxymethyl native dextran coated USPIO | 39 |
| 60 | carboxymethyl reduced dextran non-magnetic colloid | 12 |
| 43 | carboxymethyl reduced dextran coated USPIO | 0 |

The effect of the CMRD-USPIO preparations having increasing levels of carboxymethyl substitution on the extent of anaphylactic response, measured as percent edema, is shown in Table 16. The data show that a threshold level of substitution was necessary to reduce the edematous response, and that once this threshold of substitution was achieved, the decrease in response of the rats to dextran was a surprising elimination of the edematous response. That is, no edema was observed at 1,265 micromoles of carboxyl per gram.

TABLE 16

Extent of rat paw edema as a function of amount of carboxymethylation of dextran coating of USPIOs.

| Example | micromol COOH per g dextran | % edema |
|---|---|---|
| 44 | 110 | 24 |
| 45 | 130 | 54 |
| 46 | 280 | 81 |
| 47 | 450 | 37 |
| 48 | 580 | 105 |
| 43 | 1,265 | 0 |

Example 65

Toxicity of Iron Oxide Complexes with a Polyol, Polyether, or Carboxyalkylated Polyol or Polyether in Rats An anaphylaxis type of reaction to dextran has been exhibited by rats and by a small but significant fraction of the human population (Squire, J. R. et al., "Dextran, Its Properties and Use in Medicine," Charles C. Thomas, Springfield, Ill., 1955). The reaction resembles anaphylactic shock but does not require prior sensitization, and is characterized in rats by the rapid development of prostration, diffuse peripheral vasodilation, and edema of paws, snout and tongue (Voorhees, A. B. et al., *Proc. Soc. Exp. Biol. Med.* 1951, 76:254). When accompanied by barbiturate anesthesia, it produces marked hypotension and cyanosis (Hanna, C. H. et al., *Am. J. Physiol.* 1957, 191:615).

A modified procedure as described in Example 64 is used to measure the extent of rat paw edema response, as an indicator of whether the presence of iron oxide polyol or polyether complexes, or iron oxide complexes with carboxyalkyl-, amino-, amido-, ester-, derivatives of polyols or polyethers, will cause potential human adverse reactions upon intravenous injection. Rat paw edema is measured as the volume of the paw prior to and subsequent to injection of test material, using a plethysmometer, which is a differential volume measuring device. The dose of test material is injected, and a second reading is taken after a designated interval, and the percent change in paw volume is calculated. The dose administered in these studies can be up to 100 mg Fe/kg body weight, a dose much greater than that used as an imaging agent or hematinic agent in rats, pigs, and humans (see Examples 67-70) and comparable to recommended dosages for Ferrlecit® and Venofer® when used as hematinic agents (see p. 21 line 17 through p. 22, line 2, above).

For embodiments in accordance with the present invention, minimal paw edema is observed with the iron oxide polyol or polyether complexes of the present invention, as measured by the volume of the paw prior to and after parenteral administration of the complexes. This is in marked contrast to rats administered other known polyol or polyether iron oxide complexes such as Ferrlecit® or Venofer®.

Example 66

Guinea Pig Reaction Test

Similarly, a guinea pig anaphylaxis reaction test is also used as a standard test model for measuring the likelihood of anaphylactic response in humans, and is a test required by the FDA for almost all parenterally administered new compounds. In this test, guinea pigs are injected with small amounts of the test compound beneath the skin for a period of between about 6 to 8 weeks, to cause the guinea pigs to build up antibodies to the test compound and to be sensitized to the test compound. Then, a full dose of the test compound is administered to the guinea pig by parenteral administration. The full dose administered in these studies can be up to 100 mg Fe/kg body weight, a dose much greater than that used as an imaging agent or hematinic agent in rats, pigs, and humans (see Examples 67-70) and comparable to recommended dosages for Ferrlecit® and Venofer® when used as hematinic agents. For the pre-sensitization injections, the small amount of polyol or polyether iron oxide complex administered beneath the skin for 6 to 8 weeks can be from about 0.1 mg/kg body weight or less, to about 0.5-1 mg/kg body weight, depending on the individual test compound administered. If an anaphylactic response is observed, there is a strong presumption that the test compound will cause anaphylaxis in human subjects.

For embodiments in accordance with the present invention, minimal guinea pig anaphylaxis is observed with the iron oxide polyol or polyether complexes of the present invention, as measured by the incidence of guinea pig anaphylaxis to the polyol or polyether iron oxide complexes after parenteral administration following pre-sensitization. This is in marked contrast to guinea pigs administered other known polyol or polyether iron oxide complexes such as Ferrlecit® or Venofer®.

Example 67

Toxicity Studies in Rats of Reduced and Non-Reduced Dextrans

The procedure used in Example 64 was used to determine if the coating alone, that is, reduced dextrans or their derivatives rather than non-reduced native dextrans, could eliminate potential human adverse reactions upon intravenous injection. Rat paw edema was measured as the volume of the paw prior and subsequent to injection, as in Example 64. The dose administered in these studies was, as above, 100 mg test substance/kg body weight.

The results observed following administration of reduced and non-reduced T10 dextrans were similar for each material (Table 17). Reduced dextran T10 elicited the same extent of edema as native dextran T10. Elimination or decrease in edema could not be attributed merely to reduction of the dextran.

TABLE 17

Effect of native and reduced 10 kDa polysaccharides on rat edema showing mere reduction has no significant effect

| Example | test dextran | % edema |
|---|---|---|
| Dextran T-10 (commercial[a]) | native T10 | 61 |
| 12 | reduced T10 | 67 |

[a]Obtained from Pharmacia-Upjohn (Piscataway, NJ)

Table 18 shows the effect of increased levels of carboxymethyl substitution of reduced dextran on the extent of anaphylactoid response, measured as percent edema. The data show that above a threshold level of carboxymethyl substitution, edema was decreased or eliminated. For dextrans above this threshold level of substitution, the decrease in the toxic response of the rats to dextran was a surprising elimination of response, that is, no edema was observed.

TABLE 18

Relationship between rat paw edema and degree of carboxymethylation of dextran T10 preparations.

| Example | test substance | micromol COOH/g per dextran | % edema |
|---|---|---|---|
| 19 | carboxymethyl reduced | 110 | 65 |
| 20 | carboxymethyl reduced | 280 | 60 |
| 22 | carboxymethyl reduced | 450 | 56 |
| 14 | carboxymethyl reduced | 1,265 | 6 |
| 24 | carboxymethyl reduced | 1,887 | 1 |
| 25 | carboxymethyl native | 1,220 | 0 |

Example 68

Pharmacokinetics of CMRD Coated USPIO in the Rat: Blood Clearance

Three male CD® rats (Charles River Laboratories, Wilmington, Mass.; weight range 272 to 290 g) were anaesthetized intraperitoneally with a long lasting anesthetic, Inactin (100 mg per kg body weight). The femoral artery and vein were exposed by a small incision at the hip-femur joint, and the artery was cannulated with PESO tubing connected to a 1 mL syringe filled with heparinized saline (10 units per ml). To serve as a baseline, 0.25 mL of arterial blood was collected at time zero, and CMRD coated USPIO (Example 43) was injected into the femoral artery. Blood samples of 0.25 mL were collected at the times indicated in FIGS. 5 and 6.

T2 magnetic relaxation times were measured in each sample, and the relaxivity (1/T2) was calculated. First-order reaction kinetics were used to determine the half-life of the sample in the blood ($t_{1/2}$). The equation used to fit the data was:

$$1/T2 - 1/T_{baseline} = Ae^{-kt}$$

where $1/T_2$ is the relaxivity of the blood at time t post-injection; $1/T_{baseline}$ is the baseline relaxivity, and $A\,e^{-kt}$ represents the first-order decay of the test material from the blood. Taking the natural log of each side of this equation yields:

$$\ln(1/T2 - 1/T_{baseline}) = -kt + \ln A_0$$

According to this second equation, a graph of $\ln(1/T2-1/T_{baseline})$ versus time, t, should give a straight line with slope −k (the first order rate constant) and intercept $\ln A_0$ (which equals $\ln(1/T2-1/T_{baseline}$ at time zero) if the rate of removal of the USPIO from blood follows first order kinetics. FIG. 6 shows that a straight line was obtained. The half-life ($t_{1/2}$), which is the time that the amount of CMRD coated USPIO decreased to one half its amount of concentration in the blood, was determined to be 67 min, with a range of 61 to 75 min at a confidence level of 95%.

Example 69

Magnetic Resonance Imaging Using CMRD Coated USPIO in the Rat

Figure 7B:

An MRI scan of a rat taken shortly after administration of 5 mg of CMRD coated USPIO (Example 43) per kg body weight is shown in FIG. 7B. The heart, aorta, and coronary artery were found to be readily imaged using this agent. An image of the rat taken pre-administration of the agent (FIG. 7A) is included to illustrate the substantial increase in contrast effected by administration of the test substance.

Example 70

MRI of CMRD Coated USPIO in the Pig

Figure 8B:
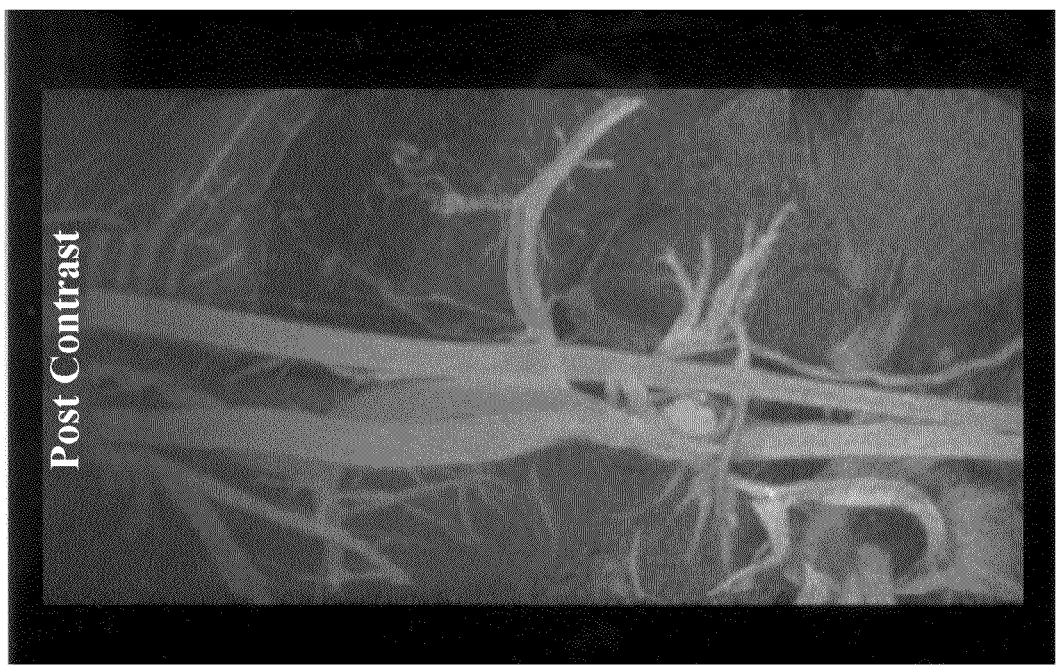
FIG. 8 shows MRI images of a pig, pre-administration (A) and post-administration (B) of contrast agent, anterior portion at top. CMRD coated USPIO (Example 43; 4 mg of iron per kg body weight) was administered into the femoral vein prior to taking the post administration contrast image. The figure illustrates enhanced visualization of the heart and surrounding arteries and veins caused by administration of CMRD coated USPIO. Imaging was performed using a Siemans 1.5T Magnatom Vision magnetic resonance imager.
Figure 9A:
FIG. 9 shows MRI images of the anterior portion of a normal human subject, pre-administration (A) and post-administration (B) of contrast imaging agent. CMRD coated USPIO (4 mg of iron per kg body weight) was administered as a bolus into a vein in the arm prior to taking the post contrast image. Imaging was performed 15 to 30 minutes after administration of contrast agent. The image illustrates enhanced visualization of the heart and surrounding arteries and veins.

FIG. 8 illustrates enhanced MRI visualization of the heart and surrounding arteries, as well as the lungs and kidneys of the pig. Four doses of 0.4, 0.8, 1.6, and 2.2 mg of iron/kg body weight of sample (Example 43) were each administered to the pig in sequential order. Each dose was followed by administration of 20 mL of physiological saline, and an MRI image was obtained after each dose. The image shown in FIG. 8B is representative of images obtained after each administration. A pre-image of the pig (FIG. 8A) is included to illustrate the substantial increase in contrast effected by the agent.

A problem associated with low molecular weight gadolinium based contrast agents is that they leak from the vascular space into the interstitial space and create a hazy background. This hazy background interferes with effective use of second or third injections of a contrast agent administered during a single examination. Such extravascular leakage might not be expected with carboxymethyl reduced dextran-coated USPIOs or similarly prepared alkoxyalkylated polyol or polyether iron oxide complexes, due to the relatively large size of the particle, compared to the size of the particles of a gadolinium contrast agent.

This expectation was confirmed by imaging of rats (Example 69) and in the data obtained by imaging of the pig (FIG. 8B). No background haze was observed following use of the CMRD USPIO compositions of the present invention. This observation enabled performance of additional vascular imaging tests, after sequential administration of additional doses. Upon intravenous administration, the CMRD coated USPIO, which is an embodiment of the invention, moved as a bolus rapidly into the arteries, organs, and veins, and achieved a uniform distribution in the blood after 20 minutes. Upon administration of a second bolus of the agent, additional good images were obtained. A third injection and a fourth injection were administered with similar results i.e., good images were obtained. Thus, the process of bolus injection and first pass application of the CMRD coated USPIO was demonstrated. Further, application of a multiple injection protocol within a reasonably short period of time after the first administration, the entire protocol being accomplished in a time period equivalent to a visit by a human subject to an imaging facility, was also demonstrated.

The principal advantages of capability of multiple bolus injections within a single examination are the opportunities to correct a deficiency in imaging that might arise after an injection, and to image multiple parts of the body during a single examination. In this manner, additional sites within the body of a subject can be imaged within a short period of time after scanning and analysis of earlier images from an earlier pass, and subsequent injections of contrast agent can be used to obtain different views, or to extend the view in one or more physical dimensions. For example, detailed analysis of the location and size of a blood clot in a limb such as a leg, can be performed using a series of views taken in the each of a first, second, and subsequent passes.

The capability for achieving additional multiple passes of administration of a composition of the invention and obtaining additional rounds of MRI data, beyond a first dose, present strong advantages of the compositions that are embodiments of the present invention. MRI analyses have in the past been limited by the physical length of the anatomical feature in need of imaging, and by the numbers of structures that can be imaged using a single detection instrument unit in a given time period.

The results obtained in pigs were observed also in human subjects (Examples 71 and 72).

Example 71

Intravenous Injection of CMRD Coated USPIO into Normal Human Subjects

The trial design employed thirty-five human subjects each administered one dose of CMRD T10 coated USPIO prepared according to Example 43(i.v.; 1-4 mg of iron/kg body weight). The objectives of Examples 71 and 72 were to examine subjects for any potential side effect of the treatment, to obtain data on the composition as an MRI contrast agent, and to determine the half-life of the composition in blood.

No adverse reactions attributable to administration of the composition were observed among the treated subjects at any dose, including the highest dose (4 mg/kg). For comparison, in clinical trials of Feridex I.V.®, approximately 2-3% of treated patients reported back pain, even though Feridex I.V.® and other comparable imaging products are administered in much smaller doses (e.g., 0.56 mg of iron/kg body weight) in order to minimize adverse events and obtain useful contrast. These data indicate that an effective dose of the CMRD coated USPIO particles of the invention is safer than an effective dose of a previously approved imaging agent, Feridex I.V.®

Example 72

Rapid Imaging Kinetics and Bio-Distribution in Human Subjects

Figure 9B:
Figure 10A:
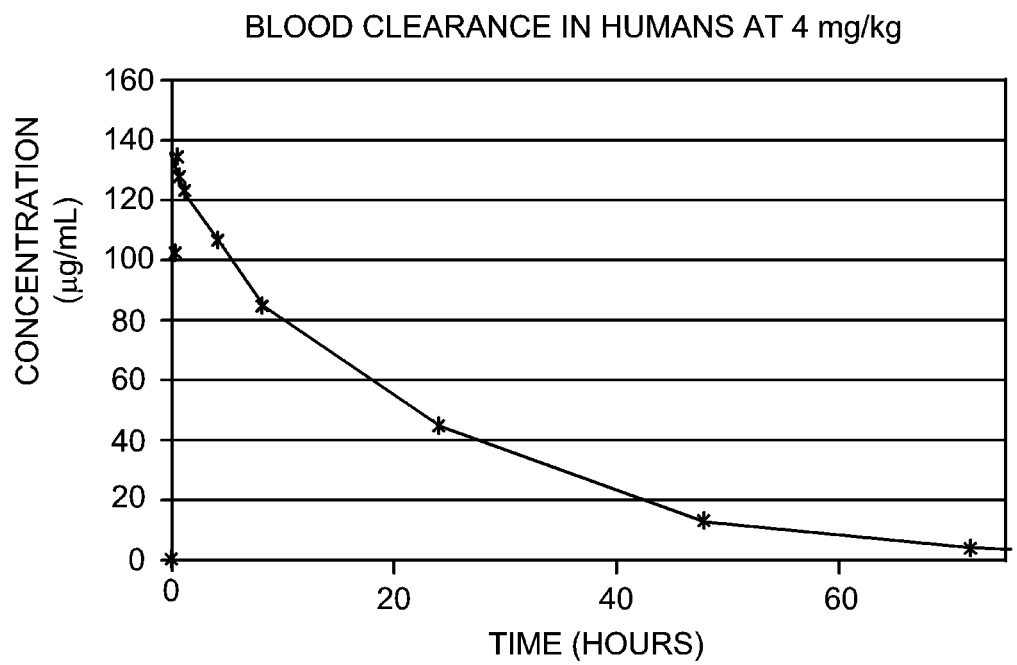
FIGS. 10A and 10B show the blood clearance kinetics in humans of imaging agent. CMRD coated USPIO (4 mg of iron per kg body weight), was administered as a bolus into a vein in the arm prior to taking blood samples. Samples were analyzed for 1/T2 relaxation to determine the blood concentration of the CMRD coated USPIO. The graph shows CMRD coated USPIO concentration (ordinate) as a function of time (abscissa).
Figure 10B:
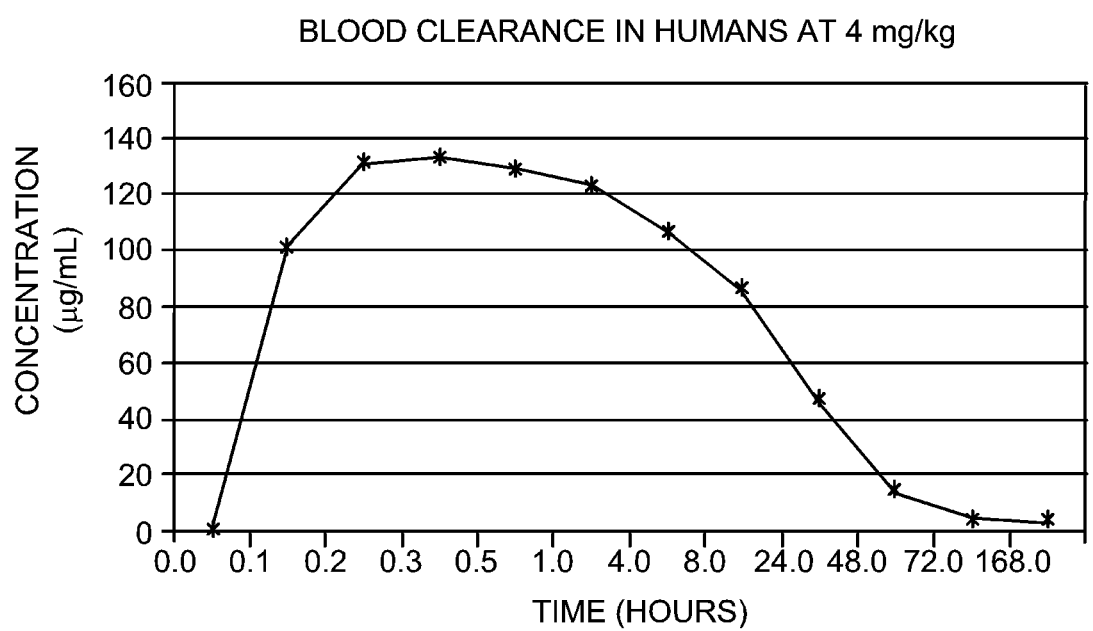

An initial intravenous bolus injection into human subjects of CMRD coated USPIO, prepared as in Example 43 1 yielded a bright MRI of the arterial portion of the circulatory system within 12 seconds post-administration (FIG. 9B). Following a further 15 seconds, MRI exposures yielded bright images of organs and veins. Equilibration of the agent throughout the vascular system was achieved within 20 minutes.

The organs capable of being imaged in the early phase following administration of the CMRD coated USPIO of the present invention included the heart, arteries and veins. Further, in addition to the larger elements of the circulatory system, the arterioles and venules of the extremities (fingers, toes) could be observed. This level of resolution allows applications to diagnosis of problems in circulation within the extremities, including the detection and localization of an area of phlebitis. Other organs that were readily imaged include the brain, kidneys, liver, spleen, and bone marrow. Lymph nodes could be imaged up to several hours after administration of an effective dose. The half-life of the agent in the blood was approximately observed to be 10-14 hours (see Table 19 and FIG. 10).

The particles ultimately were removed from circulation by being taken up by the reticuloendothelial system. During the presence of the composition at the early phase in the vascular system, and also in the late or post vascular phase in the reticuloendothelial system (RES), this composition was not observed to enter into interstitial spaces between cells. Thus, a hazy background, found to appear with usage of other compositions, for example, gadolinium based MR contract agents such as Magnevist® and DOTOREM®, is avoided during use of the CMRD-USPIO compositions, as synthesized by the methods of the Examples herein.

TABLE 19

Mean half-life of CMRD-USPIO T10 in human subjects as a function of dose.

| Dose mg iron/kg | half-life, hours | standard deviation | # subjects |
| --- | --- | --- | --- |
| 1 | 9.7 | 1.1 | 8 |
| 2 | 10.3 | 1.4 | 8 |
| 4 | 14.4 | 2.2 | 17 |

What is claimed is:

1. A method of treating a patient in need of an iron supplement, comprising intravenously administering to said patient a unit dose of an autoclaved pharmacological composition at a rate of about 1 mL/sec, wherein the composition comprises particles of a superparamagnetic iron oxide coated a carboxymethylasted reduced dextran having between about 1100 micromoles and about 1500 micromoles carboxyl per gram of carboxymethylated reduced dextran, wherein the reduced dextran has an average molecular weight of about 10 kDa, wherein the particles have a diameter between about 10 nm and 50 nm; and wherein the unit dose has about 500 mg to 600 mg of iron.

2. The method of claim 1, wherein the pharmacological composition has a free iron concentration of less than about 0.1% as determined by atomic absorption spectroscopy on a sample of the pharmacological composition filtered through a 30 K molecular weight cutoff micropartition membrane filter.

* * * * *